(12) United States Patent
Walters et al.

(10) Patent No.: US 12,404,448 B2
(45) Date of Patent: Sep. 2, 2025

(54) DIHYDROQUINOLINE PHOTOCHROMIC COMPOUNDS

(71) Applicant: TRANSITIONS OPTICAL, LTD., Tuam (IE)

(72) Inventors: Robert W. Walters, Murrysville, PA (US); Jun Deng, Mars, PA (US); Shengwen Yuan, Northbrook, IL (US)

(73) Assignee: Transitions Optical, Ltd., Tuam (IE)

( * ) Notice: Subject to any disclaimer, the term of this patent is extended or adjusted under 35 U.S.C. 154(b) by 792 days.

(21) Appl. No.: 17/763,713

(22) PCT Filed: Sep. 27, 2019

(86) PCT No.: PCT/EP2019/076256
§ 371 (c)(1),
(2) Date: Mar. 25, 2022

(87) PCT Pub. No.: WO2021/058114
PCT Pub. Date: Apr. 1, 2021

(65) Prior Publication Data
US 2022/0333004 A1    Oct. 20, 2022

(51) Int. Cl.
*C09K 9/02*    (2006.01)
*C07D 215/06*    (2006.01)
*G02C 7/10*    (2006.01)

(52) U.S. Cl.
CPC .............. *C09K 9/02* (2013.01); *C07D 215/06* (2013.01); *C09K 2211/1018* (2013.01); *G02C 7/102* (2013.01)

(58) Field of Classification Search
CPC ....................................................... C09K 9/02
USPC ....................................................... 546/110
See application file for complete search history.

(56) References Cited

U.S. PATENT DOCUMENTS

| | | | |
|---|---|---|---|
| 4,812,171 A | 3/1989 | Brettle et al. | |
| 5,391,748 A | 2/1995 | Berneth | |
| 6,248,264 B1 | 6/2001 | Clarke et al. | |
| 8,608,988 B2 | 12/2013 | Bowles et al. | |
| 9,028,728 B2 | 5/2015 | Bancroft et al. | |
| 10,371,866 B2 | 8/2019 | Frease et al. | |
| 10,954,397 B2 | 3/2021 | Haley et al. | |

FOREIGN PATENT DOCUMENTS

| | | | |
|---|---|---|---|
| DE | 4241621 A1 | 6/1994 | |
| WO | 8800223 A1 | 1/1988 | |
| WO | 9842693 A2 | 10/1998 | |
| WO | 2016142496 A1 | 9/2016 | |
| WO | 2017030545 A1 | 2/2017 | |

OTHER PUBLICATIONS

Cardellini et al., "Hydrogen Chloride Treatment of Quinolinic Aminoxyls. Part 2. Crystal Structures of 6-Chloro-1,2-dihydro-2,2-diphenyl- and 6,8-Dichloro-1,2-dihydro-2,2-diphenylquinoline", J.Chem. Soc. Perkin Trans., 1994, pp. 769-775, vol. 2.
Colonna et al., "Stable Nitroxide Radicals. Reaction between 2-Cyano- and 4Cyanobenzoquinoline N-Oxides and the Grignard Reagent", J. Heterocyclic Chem., 1980, pp. 1473-1477, vol. 17.
Gilman et al., "The Reaction of Aryllithium Compounds with 2-Arylquinolines", Journal of the American Chemical Society, Apr. 1947, pp. 877-880, vol. 69.
Kolc et al., "Photochromism of 1,2-Dihydroquinolines", Journal of the American Chemical Society, pp. 6513-6514, Nov. 1969, vol. 91:23.
Tinland et al., "A Theoretical Study of the Electronic Spectrum of Photochromic 1,2-Dihydroquinoline", Spectroscopy Letters, 1971, pp. 337-340, vol. 4.

(Continued)

*Primary Examiner* — Taofiq A Solola
(74) *Attorney, Agent, or Firm* — The Webb Law Firm

(57) ABSTRACT

The present invention relates to a photochromic compound having a core fused ring structure represented by at least one of the following Formula (Ia) or Formula (IIa), (Ia) (IIa) Independently for each of Formula (Ia) and Formula (IIa): $R^1$ is in each case independently selected from substituted or unsubstituted aryl, substituted or unsubstituted heteroaryl, $—SO_2R^5$, or $—C(O)—XR^5$, where, X is selected from a single bond, $—N(R^5)—$, or $—O—$, and $R^5$ in each case is independently selected from hydrogen, substituted or unsubstituted alkyl, substituted or unsubstituted aryl, or substituted or unsubstituted heteroaryl; and B and B' are each independently selected from substituted or unsubstituted alkenyl, substituted or unsubstituted alkynyl, substituted or unsubstituted aryl, or substituted or unsubstituted heteroaryl. The present invention also relates to photochromic compositions and articles including such photochromic compounds.

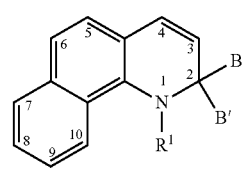

(Ia)

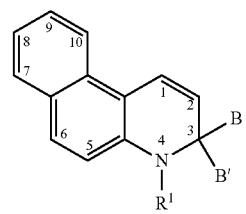

(IIa)

14 Claims, No Drawings

(56) References Cited

OTHER PUBLICATIONS

Yao et al., "Formation of a One-Dimensional Stacking Structure of π-Conjugated Nitroxyl Radical Bearing a 1,2,5-Thiadiazole Ring and Its Magnetic Property", Crystal Growth & Design, pp. 413-417, 2003, vol. 5:2.

DIHYDROQUINOLINE PHOTOCHROMIC COMPOUNDS

CROSS-REFERENCE TO RELATED APPLICATION

This application is the United States national phase of International Application No. PCT/EP2019/076256 filed Sep. 27, 2019, the disclosure of which is hereby incorporated by reference in its entirety.

FIELD

The present invention relates to photochromic compounds having a dihydroquinoline core structure and to photochromic compositions and articles including such photochromic compounds.

BACKGROUND

Photochromic compounds and materials, in response to certain wavelengths of electromagnetic radiation (or "actinic radiation"), typically undergo a transformation from one form or state to another form, with each form having a characteristic or distinguishable absorption spectrum associated therewith. Typically, upon exposure to actinic radiation, many photochromic materials are transformed from a closed-form, which corresponds to an unactivated (or bleached, or substantially colorless) state of the photochromic material, to an open-form, which corresponds to an activated (or colored) state of the photochromic material. In the absence of exposure to actinic radiation, such photochromic materials are reversibly transformed from the activated (or colored) state, back to the unactivated (or bleached) state. Compositions and articles, such as eyewear lenses, that contain photochromic materials or have photochromic materials applied thereto (such as in form of a photochromic coating composition) typically display colorless (or clear) and colored states that correspond to the colorless and colored states of the photochromic materials contained therein and/or applied thereto.

Photochromic compounds and materials are typically characterized with regard to various properties, such as photochromic properties, which include, but are not limited to, fade rate; change in optical density (sometimes designated as (ΔOD); the change in optical density (ΔOD) at saturation; sensitivity (sometimes designated as (ΔOD/Min); the efficiency at which the photochromic compound absorbs radiation required to activate the photochromic compound (sometimes designated as chromaticity); and dichroic properties (such as in the case of photochromic-dichroic compounds), which can be quantified with regard to absorption ratio (AR) values.

It would be desirable to develop new photochromic compounds. It would be further desirable that such newly developed photochromic compounds possess properties, such as photochromic properties and optionally dichroic properties, that are at least the same as or better than those of existing photochromic compounds.

SUMMARY

In accordance with the present invention, there is provided a photochromic compound having a core fused ring structure represented by at least one of the following Formula (Ia) or Formula (IIa),

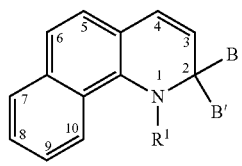

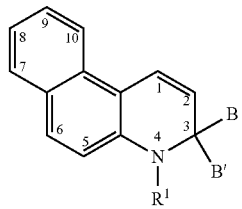

Independently for Formula (Ia) and Formula (IIa), $R^1$ is in each case independently selected from substituted or unsubstituted aryl, substituted or unsubstituted heteroaryl, $-SO_2R^5$, or $-C(O)-XR^5$, in which, X is selected from a single bond, $-N(R^5)-$, or $-O-$, and $R^5$ in each case is independently selected from hydrogen, substituted or unsubstituted alkyl, substituted or unsubstituted aryl, or substituted or unsubstituted heteroaryl. Further independently for Formulas (Ia) and (IIa), B and B' are each independently selected from substituted or unsubstituted alkenyl, substituted or unsubstituted alkynyl, substituted or unsubstituted aryl, or substituted or unsubstituted heteroaryl.

The features that characterize the present invention are pointed out with particularity in the claims, which are annexed to and form a part of this disclosure. These and other features of the invention, its operating advantages and the specific objects obtained by its use will be more fully understood from the following detailed description in which non-limiting embodiments of the invention are illustrated and described.

DETAILED DESCRIPTION

As used herein, the articles "a", "an", and "the" include plural referents unless otherwise expressly and unequivocally limited to one referent.

Unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

As used herein, unless otherwise indicated, left-to-right representations of linking groups, such as divalent linking groups, are inclusive of other appropriate orientations, such as, but not limited to, right-to-left orientations. For purposes of non-limiting illustration, the left-to-right representation of the divalent linking group

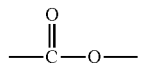

or equivalently —C(O)O—, is inclusive of the right-to-left representation thereof,

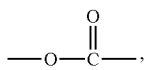

or equivalently —O(O)C— or —OC(O)—.

Other than in the operating examples, or where otherwise indicated, all numbers expressing quantities of ingredients, reaction conditions, and so forth used in the specification and claims are to be understood as modified in all instances by the term "about".

As used herein, molecular weight values of polymers, such as weight average molecular weights (Mw) and number average molecular weights (Mn), are determined by gel permeation chromatography using appropriate standards, such as polystyrene standards.

As used herein, polydispersity index (PDI) values represent a ratio of the weight average molecular weight (Mw) to the number average molecular weight (Mn) of the polymer (i.e., Mw/Mn).

As used herein, the term "polymer" means homopolymers (e.g., prepared from a single monomer species), copolymers (e.g., prepared from at least two monomer species), and graft polymers.

As used herein, the term "(meth)acrylate" and similar terms, such as "(meth)acrylic acid ester", means methacrylates and/or acrylates. As used herein, the term "(meth) acrylic acid" means methacrylic acid and/or acrylic acid.

The photochromic compounds of the present invention, as described herein, including, but not limited to, photochromic compounds represented by Formula (Ia) and Formula (IIa), in each case can optionally further include one or more coproducts, resulting from the synthesis of such compounds.

As used herein, the term "photochromic" and similar terms, such as "photochromic compound", means having an absorption spectrum for at least visible radiation that varies in response to absorption of at least actinic radiation. Further, as used herein, the term "photochromic material" means any substance that is adapted to display photochromic properties (such as, adapted to have an absorption spectrum for at least visible radiation that varies in response to absorption of at least actinic radiation) and which includes at least one photochromic compound.

As used herein, the term "actinic radiation" means electromagnetic radiation that is capable of causing a response in a material, such as, but not limited to, transforming a photochromic material from one form or state to another as will be discussed in further detail herein.

As used herein, the term "photochromic material" includes thermally reversible photochromic materials and compounds and non-thermally reversible photochromic materials and compounds. The term "thermally reversible photochromic compounds/materials" as used herein means compounds/materials capable of converting from a first state, for example a "clear state", to a second state, for example a "colored state", in response to actinic radiation, and reverting back to the first state in response to thermal energy. The term "non-thermally reversible photochromic compounds/materials" as used herein means compounds/materials capable of converting from a first state, for example a "clear state", to a second state, for example a "colored state", in response to actinic radiation, and reverting back to the first state in response to actinic radiation of substantially the same wavelength(s) as the absorption(s) of the colored state.

As used herein, to modify the term "state", the terms "first" and "second" are not intended to refer to any particular order or chronology, but instead refer to two different conditions or properties. For purposes of non-limiting illustration, the first state and the second state of a photochromic compound can differ with respect to at least one optical property, such as but not limited to the absorption of visible and/or UV radiation. Thus, according to various non-limiting embodiments disclosed herein, the photochromic compounds of the present invention can have a different absorption spectrum in each of the first and second state. For example, while not limiting herein, a photochromic compound of the present invention can be clear in the first state and colored in the second state. Alternatively, a photochromic compound of the present invention can have a first color in the first state and a second color in the second state.

As used herein, the term "optical" means pertaining to or associated with light and/or vision. For example, according to various non-limiting embodiments disclosed herein, the optical article or element or device can be chosen from ophthalmic articles, elements and devices, display articles, elements and devices, windows, mirrors, and active and passive liquid crystal cell articles, elements and devices.

As used herein, the term "ophthalmic" means pertaining to or associated with the eye and vision. Non-limiting examples of ophthalmic articles or elements include corrective and non-corrective lenses, including single vision or multi-vision lenses, which can be either segmented or non-segmented multi-vision lenses (such as, but not limited to, bifocal lenses, trifocal lenses and progressive lenses), as well as other elements used to correct, protect, or enhance (cosmetically or otherwise) vision, including without limitation, contact lenses, intra-ocular lenses, magnifying lenses, and protective lenses or visors.

As used herein, the term "display" means the visible or machine-readable representation of information in words, numbers, symbols, designs or drawings. Non-limiting examples of display elements include screens, monitors, and security elements, such as security marks.

As used herein, the term "window" means an aperture adapted to permit the transmission of radiation therethrough. Non-limiting examples of windows include automotive and aircraft transparencies, windshields, filters, shutters, and optical switches.

As used herein, the term "mirror" means a surface that specularly reflects a large fraction of incident light.

As used herein, the term "liquid crystal cell" refers to a structure containing a liquid crystal material that is capable of being ordered. A non-limiting example of a liquid crystal cell element is a liquid crystal display.

As used herein, spatial or directional terms, such as "left", "right", "inner", "outer", "above", "below", and the like, relate to the invention as described spatially, in some embodiments. It is to be understood, however, that the invention can assume various alternative orientations and, accordingly, such terms are not to be considered as limiting.

As used herein, the terms "formed over", "deposited over", "provided over", "applied over", "residing over", or "positioned over", mean formed, deposited, provided, applied, residing, or positioned on but not necessarily in direct (or abutting) contact with the underlying element, or surface of the underlying element. For example, a layer "positioned over" a substrate does not preclude the presence of one or more other layers, coatings, or films of the same or different composition located between the positioned or formed layer and the substrate.

As used herein, recitations relating to ring positions such as, but not limited to, position-x (e.g., position-3 or position-13) mean a particular position in the ring structure, such as the core skeletal structure, of a chemical compound, such as the dihydroquinoline photochromic compounds of the present invention, and which are depicted herein, in accordance with some embodiments, by numbers within the ring structures of representative chemical formulas, such as, but not limited, to Formulas (Ia) and/or (IIa).

By "core skeletal structure" is meant a compound comprising at least the skeletal structure depicted in the associated Formula. The core skeletal structure is provided for purposes of including, but not limited to, identifying numbered ring positions. It is to be understood that, unless specifically shown to the contrary, the core skeletal structure(s) can have one or more atoms or one or more groups (not specifically illustrated on the corresponding Formula) bonded to one or more of the numbered ring positions on the core skeletal structure, which can be the same or different from one another.

The photochromic compounds of the present invention are referred to herein with reference to the term "core skeletal structure", which can be represented by one or more formulas, such as but not limited to Formulas (Ia) and/or (IIa).

All documents, such as but not limited to issued patents and patent applications, referred to herein, and unless otherwise indicated, are to be considered to be "incorporated by reference" in their entirety.

As used herein, the term "aryl" and related terms, such as "aryl group", means an aromatic cyclic monovalent hydrocarbon radical. As used herein, the term "aromatic" and related terms, such as "aromatic group", means a cyclic conjugated hydrocarbon having stability (due to delocalization of pi-electrons) that is significantly greater than that of a hypothetical localized structure. Examples of aryl groups include $C_6$-$C_{14}$ aryl groups, such as, but not limited to, phenyl, naphthyl, phenanthryl, and anthracenyl.

As used herein, recitations of "halo substituted" and related terms (such as, but not limited to, haloalkyl groups, haloalkenyl groups, haloalkynyl groups, haloaryl groups, and halo-heteroaryl groups) mean a group in which at least one, and up to and including all of the available hydrogen groups thereof, is substituted with a halo group, such as but not limited to F, Cl or Br. The term "halo-substituted" is inclusive of "perhalo-substituted". As used herein, the term perhalo-substituted group and related terms (such as, but not limited to, perhaloalkyl groups, perhaloalkenyl groups, perhaloalkynyl groups, perhaloaryl groups or perhalo-heteroaryl groups) means a group in which all of the available hydrogen groups thereof are substituted with a halo group. For purposes of non-limiting illustration, perhalomethyl is —$CX_3$; and perhalophenyl is —$C_6X_5$, where X represents one or more halo groups, such as but not limited to F, Cl or Br.

As used herein, recitations of "linear or branched" groups, such as linear or branched alkyl, are herein understood to include groups that are linear (or "straight chain"), such as linear $C_1$-$C_{25}$ alkyl groups; and groups that are appropriately branched, such as branched $C_3$-$C_{25}$ alkyl groups.

The term "alkyl" as used herein means linear or branched, cyclic or acyclic $C_1$-$C_{25}$ alkyl. Linear or branched alkyl can include $C_1$-$C_{25}$ alkyl, such as $C_1$-$C_{20}$ alkyl, such as $C_2$-$C_{10}$ alkyl, such as $C_1$-$C_{12}$ alkyl, such as $C_1$-$C_6$ alkyl. Examples of alkyl groups from which the various alkyl groups of the present invention can be selected from include, but are not limited to, those recited further herein. Alkyl groups can include "cycloalkyl" groups. The term "cycloalkyl" as used herein means groups that are appropriately cyclic, such as, but not limited to, $C_3$-$C_{12}$ cycloalkyl (including, but not limited to, cyclic $C_5$-$C_7$ alkyl, or cyclic $C_3$-$C_{10}$ alkyl) groups. Examples of cycloalkyl groups include, but are not limited to, those recited further herein. The term "cycloalkyl" as used herein also includes bridged ring polycycloalkyl groups (or bridged ring polycyclic alkyl groups), such as, but not limited to, bicyclo[2.2.1]heptyl (or norbornyl) and bicyclo[2.2.2]octyl; and fused ring polycycloalkyl groups (or fused ring polycyclic alkyl groups), such as, but not limited to, octahydro-1H-indenyl, and decahydronaphthalenyl.

The term "heterocycloalkyl" as used herein means groups that are appropriately cyclic, such as, but not limited to, $C_2$-$C_{12}$ heterocycloalkyl groups, such as $C_2$-$C_{10}$ heterocycloalkyl groups, such as $C_5$-$C_7$ heterocycloalkyl groups, and which have at least one hetero atom in the cyclic ring, such as, but not limited to, O, S, N, P, and combinations thereof. Examples of heterocycloalkyl groups include, but are not limited to, imidazolyl, tetrahydrofuranyl, tetrahydropyranyl and piperidinyl. The term "heterocycloalkyl" as used herein also includes bridged ring polycyclic heterocycloalkyl groups, such as, but not limited to, 7-oxabicyclo[2.2.1]heptanyl; and fused ring polycyclic heterocycloalkyl groups, such as, but not limited to, octahydrocyclopenta[b]pyranyl, and octahydro-1H-isochromenyl.

The term "heteroaryl", as used herein, includes, but is not limited to, $C_3$-$C_{18}$ heteroaryl, such as, but not limited to, $C_3$-$C_{10}$ heteroaryl (including fused ring polycyclic heteroaryl groups) and means an aryl group having at least one hetero atom in the aromatic ring, or in at least one aromatic ring in the case of a fused ring polycyclic heteroaryl group. Examples of heteroaryl groups include, but are not limited to, furanyl, pyranyl, pyridinyl, quinolinyl, isoquinolinyl, and pyrimidinyl.

As used herein, the term "fused ring polycyclic-aryl-alkyl group" and similar terms, such as fused ring polycyclic-alkyl-aryl group, fused ring polycyclo-aryl-alkyl group, and fused ring polycyclo-alkyl-aryl group, means a fused ring polycyclic group that includes at least one aryl ring and at least one cycloalkyl ring that are fused together to form a fused ring structure. For purposes of non-limiting illustration, examples of fused ring polycyclic-aryl-alkyl groups include, but are not limited to, indenyl, 9H-flourenyl, cyclopentanaphthenyl, and indacenyl.

The term "aralkyl", as used herein, includes, but is not limited to, $C_6$-$C_{24}$ aralkyl, such as, but not limited to, $C_6$-$C_{10}$ aralkyl, and means an alkyl group substituted with an aryl group. Examples of aralkyl groups include, but are not limited to, benzyl and phenethyl.

Representative alkyl groups include, but are not limited to, methyl, ethyl, propyl, isopropyl, butyl, isobutyl, sec-butyl, tert-butyl, pentyl, neopentyl, hexyl, heptyl, octyl, nonyl and decyl. Representative alkenyl groups include, but are not limited to, vinyl, allyl, and propenyl. Representative alkynyl groups include, but are not limited to, ethynyl, 1-propynyl, 2-propynyl, 1-butynyl, and 2-butynyl. Representative cycloalkyl groups include, but are not limited to, cyclopropyl, cyclobutyl, cyclopentyl, cyclohexyl, and cyclooctyl.

The term "nitrogen-containing heterocycle", such as "nitrogen-containing heterocycle group" or nitrogen-containing heterocycle substituent", as used herein, includes, but is not limited to, a nitrogen-containing ring in which the nitrogen-containing ring is bonded through a ring nitrogen. Examples of nitrogen-containing heterocycles include, but are not limited to, cyclic aminos, such as morpholino, piperidino, and pyrrolidino; and heteroaromatics, such as imidazole, pyrrole, indole, and carbazole.

As used herein, recitations of "substituted" group, means a group including, but not limited to, alkyl group, heterocycloalkyl group, aryl group, and/or heteroaryl group, in which at least one hydrogen thereof has been replaced or substituted with a group that is other than hydrogen, such as, but not limited to, alkoxy groups; halo groups (e.g., F, Cl, I, and Br); hydroxyl groups; thiol groups; alkylthio groups; arylthio groups; ketone groups; aldehyde groups; ester groups; carboxylic acid groups; phosphoric acid groups; phosphoric acid ester groups; sulfonic acid groups; sulfonic acid ester groups; nitro groups; cyano groups; alkyl groups (including aralkyl groups); alkenyl groups; alkynyl groups; haloalkyl groups; perhaloalkyl groups; heterocycloalkyl groups; aryl groups (including alkaryl groups, including hydroxyl substituted aryl, such as phenol, and including poly-fused-ring aryl); heteroaryl groups (including poly-fused-ring heteroaryl groups); amino groups, such as —N($R^{11'}$)($R^{12'}$) where $R^{11'}$ and $R^{12'}$ are each independently selected from, for example, hydrogen, alkyl, heterocycloalkyl, aryl, or heteroaryl; carboxylate groups; siloxane groups; alkoxysilane groups; polysiloxane groups; amide groups; carbamate groups; carbonate groups; urea groups; polyester groups; polyether groups; polycarbonate groups; polyurethane groups; acrylate groups; methacrylate groups; nitrogen-containing heterocycles; or combinations thereof, including those classes and examples as described further herein.

As used herein, "at least one of" is synonymous with "one or more of", whether the elements are listed conjunctively or disjunctively. For example, the phrases "at least one of A, B, and C" and "at least one of A, B, or C" each mean any one of A, B, or C, or any combination of any two or more of A, B, or C. For example, A alone; or B alone; or C alone; or A and B; or A and C; or B and C; or all of A, B, and C.

As used herein, "selected from" is synonymous with "chosen from" whether the elements are listed conjunctively or disjunctively. Further, the phrases "selected from A, B, and C" and "selected from A, B, or C" each mean any one of A, B, or C, or any combination of any two or more of A, B, or C. For example, A alone; or B alone; or C alone; or A and B; or A and C; or B and C; or all of A, B, and C.

The discussion of the invention herein may describe certain features as being "particularly" or "preferably" within certain limitations (e.g., "preferably", "more preferably", or "even more preferably", within certain limitations). It is to be understood that the invention is not limited to or by these particular or preferred limitations, but encompasses the entire scope of the disclosure.

As used herein, and in accordance with some embodiments, the term "(meth)acrylate" such as with regard to groups, and substituents of various groups, of the photochromic compounds of the present invention, and related terms, such as "(meth)acrylate group" and "(meth)acrylate substituent", includes a material represented by —O—C(O)—C(R')=$CH_2$, where R' is hydrogen or methyl.

As used herein, and in accordance with some embodiments, the term "boronic acid" such as with regard to groups, and substituents of various groups, of the photochromic compounds of the present invention, and related terms, such as "boronic acid group" and "boronic acid substituent", includes a material represented by —B(OH)$_2$.

As used herein, and in accordance with some embodiments, the term "boronic acid ester" such as with regard to groups, and substituents of various groups, of the photochromic compounds of the present invention, and related terms, such as "boronic acid ester group" and "boronic acid ester substituent", includes a material represented by —B(OR)$_2$, where each R is independently selected from those groups as described below, other than hydrogen; or

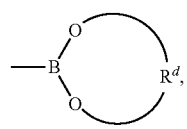

where $R^d$ is substituted or unsubstituted divalent alkyl.

As used herein, and in accordance with some embodiments, the term "ketone" such as with regard to groups, and substituents of various groups, of the photochromic compounds of the present invention, and related terms, such as "ketone group" and "ketone substituent", includes a material represented by —C(O)R, where R is selected from those groups as described below, other than hydrogen.

As used herein, and in accordance with some embodiments, the term "carboxylic acid" such as with regard to groups, and substituents of various groups, of the photochromic compounds of the present invention, and related terms, such as "carboxylic acid group" and "carboxylic acid substituent", includes a material represented by —C(O)OH.

As used herein, and in accordance with some embodiments, the term "ester" such as with regard to groups, and substituents of various groups, of the photochromic compounds of the present invention, and related terms, such as "ester group" and "ester substituent", means a carboxylic acid ester group represented by —C(O)OR, where R is selected from those groups as described below, other than hydrogen.

As used herein, and in accordance with some embodiments, the term "carboxylate" such as with regard to groups, and substituents of various groups, of the photochromic compounds of the present invention, and related terms, such as "carboxylate group" and "carboxylate substituent", includes a material represented by —OC(O)R, where R is selected from those groups as described below.

As used herein, and in accordance with some embodiments, the term "amide" such as with regard to groups, and substituents of various groups, of the photochromic compounds of the present invention, and related terms, such as "amide group" and "amide substituent", includes a material represented by —C(O)N(R)(R) or —N(R)C(O)R, where each R is independently selected from those groups as described below.

As used herein, and in accordance with some embodiments, the term "carbonate" such as with regard to groups, and substituents of various groups, of the photochromic compounds of the present invention, and related terms, such as "carbonate group" and "carbonate substituent", includes a material represented by —OC(O)OR, where R is selected from those groups as described below, other than hydrogen.

As used herein, and in accordance with some embodiments, the term "carbamate" such as with regard to groups, and substituents of various groups, of the photochromic compounds of the present invention, and related terms, such as "carbamate group" and "carbamate substituent", includes a material represented by —OC(O)N(R)(H) or —N(H)C(O)

OR, where R in each case is independently selected from those groups as described below, other than hydrogen.

As used herein, and in accordance with some embodiments, the term "urea" such as with regard to groups, and substituents of various groups, of the photochromic compounds of the present invention, and related terms, such as "urea group" and "urea substituent", includes a material represented by —N(R)C(O)N(R)(R), where each R is independently selected from those groups as described below.

As used herein, and in accordance with some embodiments, the term "siloxy" such as with regard to groups, and substituents of various groups, of the photochromic compounds of the present invention, and related terms, such as "siloxy group" and "siloxy substituent", includes a material represented by —O—Si(R)$_3$ where each R is independently selected from those groups as described below, other than hydrogen.

As used herein, and in accordance with some embodiments, the term "alkoxysilane" such as with regard to groups, and substituents of various groups, of the photochromic compounds of the present invention, and related terms, such as "alkoxysilane group" and alkoxysilane substituent", includes a material represented by —Si(OR")$_w$(R)$_t$, where w is 1 to 3 and t is 0 to 2, provided the sum of w and t is 3; R" for each w is independently selected from alkyl; and R for each t is independently selected from those groups as described below, other than hydrogen.

As used herein, and in accordance with some embodiments, the term "polysiloxane" such as with regard to groups, and substituents of various groups, of the photochromic compounds of the present invention, and related terms, such as "polysiloxane group" and "polysiloxane substituent", includes a material represented by the following Formula (B):

(B)

With reference to Formula (B): t' is greater than or equal to 2, such as from 2 to 200; $R^a$ and $R^b$ for each t' are each independently selected from a group R as described below, other than hydrogen; and $R^c$ is independently a group R as described below.

Unless otherwise stated, each R group of each of the above described boronic acid ester, ketone, ester (carboxylic acid ester), carboxylate, amide, carbonate, carbamate, urea, siloxane, alkoxysilane groups, and polysiloxane groups, is in each case independently selected from hydrogen, alkyl, haloalkyl, perhaloalkyl, cycloalkyl, heterocycloalkyl, aryl, heteroaryl, and combinations thereof.

The dihydroquinoline photochromic compounds according to the present invention, such as but not limited to those represented by Formulas (Ia), (IIa), (Ib), and (IIb), and the various groups thereof are described in further detail herein as follows. The present invention comprises, consists essentially of, or consists of, one or more aspects as described in further detail herein, in any combination.

The photochromic compounds according to the present invention can be represented by one or more core skeletal structures, such as Formulas (Ia) and (IIa), in which each available numbered ring position (such as, 1, 2, 3, 4, 5, 6, 7, 8, 9, and 10) of the core skeletal structure can independently have covalently bonded thereto, unless otherwise specified, hydrogen or a group other than hydrogen, such as those groups as described herein.

With some embodiments, the photochromic compound according to the present invention is represented by at least one of the following Formula (Ib) or Formula (IIb),

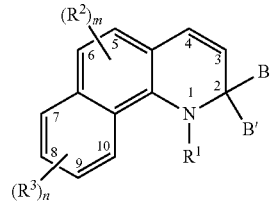

(Ib)

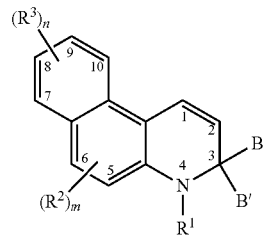

(IIb)

With reference to and independently for Formula (Ib) and Formula (IIb), m in each case is independently 0 to 2 (such as 0, 1, or 2), and n in each case is independently 0 to 4 (such as 0, 1, 2, 3, or 4).

With reference to and independently for Formula (Ib) and Formula (IIb), and for purposes of non-limiting illustration, when subscript m is less than 2, a hydrogen (—H) is bonded to each position to which an $R^2$ is not bonded. For purposes of further non-limiting illustration, and independently for Formula (Ib) and Formula (IIb), when subscript m is 0, a hydrogen (—H) is bonded to each of positions 5 and 6. For purposes of non-limiting illustration, and independently for Formula (Ib) and Formula (IIb), when subscript n is less than 4, a hydrogen (—H) is bonded to each position to which an $R^3$ is not bonded. For purposes of further non-limiting illustration, and independently for Formula (Ib) and Formula (IIb), when subscript n is 0, a hydrogen (—H) is bonded to each of positions 7, 8, 9, and 10.

With reference to and independently for Formula (Ib) and Formula (IIb), $R^2$ independently for each m, and $R^3$ independently for each n, are each independently selected from hydroxyl; cyano; (meth)acrylate; amino or nitrogen-containing heterocycle; a halo group; a perhalogenated group; substituted or unsubstituted alkyl; substituted or unsubstituted alkenyl; substituted or unsubstituted alkynyl; substituted or unsubstituted heterocycloalkyl; substituted or unsubstituted aryl; substituted or unsubstituted heteroaryl; boronic acid or boronic acid ester; substituted or unsubstituted alkoxy or substituted or unsubstituted aryloxy; substituted or unsubstituted alkylthio or substituted or unsubstituted arylthio; ketone, aldehyde, carboxylic acid ester, carboxylic acid, carboxylate, or amide; carbonate, carbamate, or urea; polyether, polyester, polycarbonate, or polyurethane; and siloxy, alkoxysilane, or polysiloxane.

With reference to and independently for Formula (Ib) and Formula (IIb), and in accordance with some embodiments, two adjacent $R^2$ groups at position-5 and position-6 together form a substituted or unsubstituted fused benzene ring, or a substituted or unsubstituted fused indeno ring. With some further embodiments, when two adjacent $R^2$ groups at position-5 and position-6 together form a substituted or unsubstituted fused indeno ring, the five-membered ring portion of the indeno ring is fused across position-5 and position-6.

In accordance with some embodiments, and independently for $R^1$ (such as independently for each of Formulas (Ia), (IIa), (Ib), and (IIb)) each aryl substituent, and each heteroaryl substituent, is in each case independently selected from halo, cyano, nitro, alkyl, alkenyl, alkynyl, haloalkyl, perhaloalkyl, heterocycloalkyl, aryl, heteroaryl, hydroxyl, thiol, alkyl ether, alkyl thioether, aryl ether, aryl thioether, ketone, aldehyde, carboxylic acid ester, carboxylic acid, carboxylate, siloxy, alkoxysilane, polysiloxane, amide, amino, nitrogen-containing heterocycle, carbamate, carbonate, urea, polyester group, polyether group, polycarbonate group, polyurethane group, an acrylate group, a methacrylate group, combinations thereof, or two or more thereof.

In accordance with some further embodiments, and independently for $R^5$ (such as independently for each of Formulas (Ia), (IIa), (Ib), and (IIb)) each alkyl substituent, each aryl substituent, and each heteroaryl substituent, is in each case independently selected from halo, cyano, nitro, alkyl, alkenyl, alkynyl, haloalkyl, perhaloalkyl, heterocycloalkyl, aryl, heteroaryl, hydroxyl, thiol, alkyl ether, alkyl thioether, aryl ether, aryl thioether, ketone, aldehyde, carboxylic acid ester, carboxylic acid, carboxylate, siloxy, alkoxysilane, polysiloxane, amide, amino, nitrogen-containing heterocycle, carbamate, carbonate, urea, polyester group, polyether group, polycarbonate group, polyurethane group, an acrylate group, a methacrylate group, combinations thereof, or two or more thereof.

In accordance with some further embodiments, and independently for $R^2$ and $R^3$ (such as independently for each of Formulas (Ib) and (IIb)) each alkyl substituent, each alkenyl substituent, each alkynyl substituent, each aryl substituent, each heterocycloalkyl substituent, each heteroaryl substituent, each alkoxy substituent, each aryloxy substituent, each alkylthio substituent, each arylthio substituent, each fused benzene ring substituent, and each fused indeno ring substituent, is in each case independently selected from halo, cyano, nitro, alkyl, alkenyl, alkynyl, haloalkyl, perhaloalkyl, heterocycloalkyl, aryl, heteroaryl, hydroxyl, thiol, alkyl ether, alkyl thioether, aryl ether, aryl thioether, ketone, aldehyde, carboxylic acid ester, carboxylic acid, carboxylate, siloxy, alkoxysilane, polysiloxane, amide, amino, nitrogen-containing heterocycle, carbamate, carbonate, urea, polyester group, polyether group, polycarbonate group, polyurethane group, an acrylate group, a methacrylate group, combinations thereof, or two or more thereof.

Independently for Formulas (Ib) and (IIb), and in accordance with some embodiments, B and B' are each independently selected from substituted phenyl or unsubstituted phenyl.

In accordance with some embodiments, independently for B and B', and independently for Formulas (Ib) and (IIb), each phenyl substituent is independently selected from alkyl, halo, perhaloalkyl, hydroxyl, thiol, alkyl ether, phenyl ether, alkyl thioether, phenyl thioether, morpholino, thiomorpho lino, piperidino, piperazino, N-alkylpiperazino, or N-phenylpiperizino.

With reference to Formulas (Ia), (IIa), (Ib), and (IIb), and in accordance with some embodiments of the present invention, $R^1$ is in each case independently selected from substituted or unsubstituted phenyl, and —C(O)—$XR^5$. The X of —C(O)—$XR^5$ of $R^1$, with some embodiments, is selected from a single bond, —N($R^5$)—, or —O—, and $R^5$ is in each case is independently selected from hydrogen or substituted or unsubstituted phenyl. Each phenyl substituent of $R^1$ and each phenyl substituent of $R^5$ is in each case independently selected from halo, cyano, nitro, alkyl, alkenyl, alkynyl, haloalkyl, perhaloalkyl, heterocycloalkyl, aryl, heteroaryl, hydroxyl, thiol, alkyl ether, alkyl thioether, aryl thioether, ketone, aldehyde, carboxylic acid ester, carboxylic acid, carboxylate, siloxy, alkoxysilane, polysiloxane, amide, amino, nitrogen-containing heterocycle, carbamate, carbonate, urea, polyester group, polyether group, polycarbonate group, polyurethane group, an acrylate group, a methacrylate group, combinations thereof, and two or more thereof.

With some further embodiments, each phenyl substituent of $R^1$ and each phenyl substituent of $R^5$ is in each case independently selected from halo, alkyl, perhaloalkyl, and alkyl ether. In accordance with some additional embodiments, $R^2$ independently for each m, and $R^3$ independently for each n, are each independently selected from alkyl, perhaloalkyl, alkyl ether, unsubstituted phenyl, and phenyl substituted with at least one substituent selected from alkyl, perhaloalkyl, or alkyl ether. In accordance with some alternative embodiments, two adjacent $R^2$ groups at position-5 and position-6 (independently for Formula (Ib) and Formula (IIb)) together form a substituted or unsubstituted fused benzene ring, where each fused benzene ring substituent is independently selected from halo, alkyl, perhaloalkyl, or alkyl ether.

With some embodiments of the photochromic compounds according to the present invention, such as represented by Formula (Ib) and/or Formula (IIb), B and B' are each independently selected from substituted or unsubstituted phenyl, wherein each phenyl substituent of B and B' is independently selected from halo, alkyl, perhaloalkyl, hydroxyl, alkyl ether, phenyl ether, morpholino, piperidino, piperazino, N-alkylpiperazino, or N-phenylpiperizino.

The present invention also provides, with some embodiments, a photochromic compound represented by the following Formula (IV):

Formula (IV)

With reference to Formula (IV), subscript n' is at least 2, such as from 2 to 100, or from 2 to 50, or from 2 to 25, or from 2 to 20, or from 2 to 15, or from 2 to 10, or from 2 to 8, or from 2 to 5, or from 2 to 4, or 2 or 3, in each case inclusive of the recited values.

With further reference to Formula (IV), the PC group or moiety, independently for each n', is a residue of a photochromic compound according to the present invention, such as represented by Formula (Ia), Formula (IIa), Formula (Ib), and/or Formula (IIb), and as described previously herein.

With additional reference to Formula (IV), $L^y$ is a multivalent linking group selected from (i) a first multivalent compound that is a multivalent polymer; and (ii) a second multivalent compound that is different than the first multivalent compound, the second multivalent compound being non-polymeric and comprising a residue selected from a residue of a polyisocyanate, a residue of a polyol, a residue of a polycarboxylic acid, a residue of a polycarbonate functional material, and combinations thereof. As used herein, the term "non-polymeric" with regard to the second multivalent compound, from which $L^y$ of Formula (IV) can be selected, means it is free of repeating monomer units (or repeating monomer residues).

In accordance with some embodiments, and with further reference to Formula (IV), the multivalent polymer of the first multivalent compound, from which $L^y$ can be selected, is selected from multivalent polyurethane, multivalent polyester, multivalent polyether, multivalent poly(meth)acrylate, multivalent polyvinylalcohol, multivalent polycarbonate, multivalent polysiloxane, and multivalent cyclic polysiloxane. The multivalent polymers from which $L^y$ can be selected can be prepared in accordance with art-recognized methods from art-recognized materials including, but not limited to, art-recognized monomers. With some embodiments, (a) at least some of the monomers from which the polymer is prepared (and of which $L^y$ is a residue) have covalently bonded thereto one or more photochromic compounds according to the present invention; and/or (b) the resulting polymer (of which $L^y$ is a residue) is subsequently modified to include photochromic compounds according to the present invention bonded thereto. The multivalent polymers from which $L^y$ can be selected can, with some embodiments, have any suitable backbone architecture, such as but not limited to, alternating backbone architecture, block backbone architecture, random backbone architecture, and combinations thereof. The multivalent polymers from which $L^y$ can be selected can, with some further embodiments, have any suitable macro polymer architecture, such as but not limited to linear polymer architecture, branched polymer architecture, comb polymer architecture, star polymer architecture, dendritic polymer architecture, and combinations thereof.

Classes of polyisocyanates that can be a residue of the second multivalent compound, from which $L^y$ of Formula (IV) can be selected, include, but are not limited to, aliphatic polyisocyanates, aromatic polyisocyanates, cycloaliphatic polyisocyanates, and heterocyclic polyisocyanates, in each case having at least 2 isocyanate groups, dimers of such polyisocyanates, trimers of such polyisocyanates, and mixtures of such polyisocyanates. Examples of polyisocyanates that can be a residue of the second multivalent compound, from which $L^y$ of Formula (IV) can be selected, include, but are not limited to, toluene-2,4-diisocyanate; toluene-2,6-diisocyanate; diphenyl methane-4,4'-diisocyanate; diphenyl methane-2,4'-diisocyanate; para-phenylene diisocyanate; biphenyl diisocyanate; 3,3'-dimethyl-4,4'-diphenylene diisocyanate; tetramethylene-1,4-diisocyanate; hexamethylene-1,6-diisocyanate; 2,2,4-trimethyl hexane-1,6-diisocyanate; lysine methyl ester diisocyanate; bis(isocyanato ethyl)fumarate; isophorone diisocyanate; ethylene diisocyanate; dodecane-1,12-diisocyanate; cyclobutane-1,3-diisocyanate; cyclohexane-1,3-diisocyanate; cyclohexane-1,4-diisocyanate; methyl cyclohexyl diisocyanate; hexahydrotoluene-2,4-diisocyanate; hexahydrotoluene-2,6-diisocyanate; hexahydrophenylene-1,3-diisocyanate; hexahydrophenylene-1,4-diisocyanate; p erhydrodiphenylmethane-2,4'-diisocyanate; perhydrodiphenylmethane-4,4'-diisocyanate, dimers thereof, trimers thereof, and mixtures thereof.

Classes of polyols that can be a residue of the second multivalent compound, from which $L^y$ of Formula (IV) can be selected, include, but are not limited to, aliphatic polyols, aromatic polyols, cycloaliphatic polyols, and heterocyclic polyols, in each case having at least 2 hydroxyl groups. Examples of polyols that can be a residue of the second multivalent compound, from which $L^y$ of Formula (IV) can be selected, include, but are not limited to, trimethylolpropane, di(trimethylolpropane), trimethylolethane, di(trimethylolethane), trishydroxyethylisocyanurate, pentaerythritol, di(pentaerythritol) ethylene glycol, propylene glycol, trimethylene glycol, butanediol, heptanediol, hexanediol, octanediol, 4,4'-(propane-2,2-diyl)dicyclohexanol, 4,4'-methylenedicyclohexanol, neopentyl glycol, 2,2,3-trimethylpentane-1,3-diol, 1,4-dimethylolcyclohexane, 2,2,4-trimethylpentane diol, 4,4'-(propane-2,2-diyl)diphenol, and 4,4'-methylenediphenol.

Classes of polycarboxylic acids that can be a residue of the second multivalent compound, from which $L^y$ of Formula (IV) can be selected, include, but are not limited to, aliphatic polycarboxylic acids, aromatic polycarboxylic acids, cycloaliphatic polycarboxylic acids, and heterocyclic polycarboxylic acids, in each case having at least 2 carboxylic acid groups and/or carboxylic acid ester groups. Examples of polycarboxylic acids that can be a residue of the second multivalent compound, from which $L^y$ of Formula (IV) can be selected, include, but are not limited to, benzene-1,2,4-tricarboxylic acid, phthalic acid, tetrahydrophthalic acid, hexahydrophthalic acid, endobicyclo-2,2,1,5-heptyne-2,3-dicarbo xylic acid, tetrachlorophthalic acid, cyclohexanedioic acid, succinic acid, isophthalic acid, terephthalic acid, azelaic acid, maleic acid, trimesic acid, 3,6-dichlorophthalic acid, adipic acid, sebacic acid, and like multifunctional carboxylic acids.

Classes of polycarbonate functional materials/compounds that can be a residue of the second multivalent compound, from which $L^y$ of Formula (IV) can be selected, include, but are not limited to, aliphatic polycarbonate functional compounds, aromatic polycarbonate functional compounds, cycloaliphatic polycarbonate functional compounds, and heterocyclic polycarbonate functional compounds, in each case having at least 2 cyclic carbonate groups. The polycarbonate functional compounds can be prepared in accordance with art-recognized methods. In accordance with some embodiments, the polycarbonate functional compounds are prepared by heating oxirane functional precursor materials in the presence of carbon dioxide and an appropriate catalyst, such as a tetraalkyl ammonium iodide and/or tetraalkyl ammonium bromide, for example, tetrabutylammonium iodide and/or tetrabutylammonium bromide. In accordance with some further embodiments, the oxirane functional precursor material is prepared by reacting one more of a polyol with at least two moles of epichlorohydrin, so as to convert at least two of the hydroxyl groups of the polyol to oxirane functional groups. The polyol can, with some embodiments, be selected from those classes and examples of polyols as recited previously herein with regard to $L^y$.

Photochromic compounds according to the present invention can be prepared in accordance with art-recognized methods. With some embodiments, the photochromic compounds according to the present invention are prepared in accordance with the synthetic procedures as described in the Examples further herein.

In accordance with the present invention, there is also provided a photochromic composition, which includes at least one photochromic compound according to the present invention, such as represented by Formulas (Ia), (Ib), (IIa), and/or (IIb), as described previously herein.

In accordance with some embodiments of the present invention, the photochromic composition includes (i) an organic material, in which the organic material is at least one of a polymeric material, an oligomeric material, and/or a monomeric material; and (ii) a photochromic compound according to the present invention, which is incorporated into at least a portion of the organic material. The photochromic compound can be incorporated into a portion of the organic material by methods including, but not limited to, at least one of blending and/or bonding the photochromic compound with the organic material or a precursor of the organic material. As used herein with reference to the incorporation of photochromic compounds into an organic material, the terms "blending" and "blended" mean that the photochromic compound/material is intermixed or intermingled with at least a portion of the organic material, but not bonded to the organic material. Further, as used herein with reference to the incorporation of photochromic compounds into an organic material, the terms "bonding" or "bonded" mean that the photochromic compound/material is linked, such as by one or more covalent bonds, to a portion of the organic material or a precursor thereof. For example, although not limiting herein, the photochromic material can be linked to the organic material through a reactive substituent.

In accordance with some embodiments of the present invention, when the organic material is a polymeric material, the photochromic compound can be incorporated into at least a portion of the polymeric material or at least a portion of the monomeric material or oligomeric material from which the polymeric material is formed. For example, photochromic compound(s) according to the present invention that have a reactive substituent can be bonded to an organic material such as a monomer, oligomer, or polymer having a group with which a reactive moiety may be reacted, or the reactive moiety can be reacted as a co-monomer in the polymerization reaction from which the organic material is formed, for example, in a co-polymerization process.

As discussed above, the photochromic compositions according to present invention can include an organic material chosen from a polymeric material, an oligomeric material and/or a monomeric material, with some embodiments. Examples of polymeric materials that can be used with the photochromic compositions of the present invention include, but are not limited to, poly(carbonate), copolymers of ethylene and vinyl acetate; copolymers of ethylene and vinyl alcohol; copolymers of ethylene, vinyl acetate, and vinyl alcohol (such as those that result from the partial saponification of copolymers of ethylene and vinyl acetate); cellulose acetate butyrate; poly(urethane); poly(acrylate); poly(methacrylate); epoxies; aminoplast functional polymers; poly(anhydride); poly(urea urethane); N-alkoxymethyl (meth)acrylamide functional polymers;

poly(siloxane); poly(silane); and combinations and mixtures thereof. Further classes and examples of polymeric materials that can be used with the photochromic compositions of the present invention include, but are not limited to, those disclosed at column 39, line 45 through column 40, line 67 of U.S. Pat. No. 9,028,728 B2, which disclosure is specifically incorporated herein by reference.

With some further embodiments, the photochromic composition of the present invention further includes at least one of a complementary photochromic material (including one or more of those other photochromic materials and compounds described further herein), a photoinitiator, a thermal initiator, a polymerization inhibitor, a solvent, a light stabilizer, a heat stabilizer, a mold release agent, a rheology control agent, a leveling agent, a free radical scavenger, and/or an adhesion promoter.

Classes of other photochromic compounds that can be used in combination with the photochromic compounds of the present invention include, but are not limited to, thermally reversible photochromic compounds, non-thermally reversible photochromic compounds, and mixtures or combinations thereof. Examples of classes of other photochromic compounds that can be used in combination with the photochromic compounds of the present invention include, but are not limited to, indeno-fused naphthopyrans, naphtho[1,2-b]pyrans, naphtho[2,1-b]pyrans, spirofluoroeno [1,2-b] pyrans, phenanthrenopyrans, quinolinopyrans, fluoroanthenopyrans, spiropyrans, benzoxazines, naphthoxazines, spiro(indoline)naphthoxazines, spiro(indoline) pyridobenzoxazines, spiro(indoline)fluoranthenoxazines, spiro(indoline)quinoxazines, fulgides, fulgimides, diarylethenes, diarylalkylethenes, diarylalkenylethenes, and mixtures thereof. Further examples of other photochromic compounds that can be used in combination with the photochromic compounds of the present invention include, but are not limited to, those disclosed at column 34, line 20 through column 35, line 13 of U.S. Pat. No. 9,028,728 B2, which disclosure is specifically incorporated by reference herein.

In accordance with some embodiments, the photochromic composition according to the present invention is a photochromic coating composition. Photochromic coating compositions according to some embodiments of the present invention include a photochromic material according to the present invention, such as described previously herein with regard to Formula (Ia), (Ib), (IIa), or (IIb); a resin composition that is optionally curable; and optionally a solvent. The photochromic coating composition can be in the form of art-recognized liquid coatings and powder coatings. The photochromic coating compositions of the present invention can be thermoplastic or thermosetting coating compositions. In an embodiment, the photochromic coating composition is a curable or thermosetting coating composition.

The curable resin composition of the curable photochromic coating compositions according to some embodiments of the present invention include a first reactant (or component) having functional groups, e.g., an epoxide functional polymer reactant; and a second reactant (or component) that is a crosslinking agent having functional groups that are reactive towards and that can form covalent bonds with the functional groups of the first reactant. The first and second reactants of the curable resin composition of the curable photochromic coating composition can each independently include one or more functional species, and are each present in amounts sufficient to provide cured photochromic coatings having a desirable combination of physical properties, e.g., smoothness, optical clarity, solvent resistance, and hardness.

Examples of curable resin compositions that can be used with the curable photochromic coating compositions according to the present invention include, but are not limited to, curable resin compositions including epoxide functional polymer (e.g., (meth)acrylic polymers containing residues of glycidyl (meth)acrylate) and epoxide reactive crosslinking agent (e.g., containing active hydrogens, such as hydroxyls, thiols and amines); and curable resin compositions including active hydrogen functional polymer (e.g., hydroxy, thiol, and/or amine functional polymer) and capped (or blocked) isocyanate functional crosslinking agent. By "capped (or blocked) isocyanate functional crosslinking agent" is meant a crosslinking agent having two or more capped isocyanate groups that can decap (or deblock) under cure conditions (e.g., at elevated temperature) to form free isocyanate groups and free capping groups. The free isocyanate groups formed by decapping of the crosslinking agent are preferably capable of reacting and forming substantially permanent covalent bonds with the active hydrogen groups of the active hydrogen functional polymer (e.g., with the hydroxy groups of a hydroxy functional polymer). Further examples of curable resin compositions that can be used with the curable photochromic coating compositions according to the present invention include, but are not limited to, those disclosed in paragraphs [0176] through [0190] of WO 2016/142496 A1; and paragraphs [0005], [0037] through [0056] through

[0059], and [0063] through [0065] of WO 2017/030545 A1, which disclosures are specifically incorporated herein by reference.

Curable photochromic coating compositions according to the present invention can, with some embodiments, optionally contain additives such as waxes for flow and wetting, flow control agents, e.g., poly(2-ethylhexyl)acrylate, adjuvant resin to modify and optimize coating properties, antioxidants and ultraviolet (UV) light absorbers. Examples of useful antioxidants and UV light absorbers include those available commercially from BASF under the trademarks IRGANOX and TINUVIN. These optional additives, when used, are typically present in amounts up to 20 percent by weight (e.g., from 0.5 to 10 percent by weight), based on total weight of resin solids of the curable resin composition.

Photochromic compositions, photochromic articles and photochromic coating compositions according to the present invention can, with some embodiments, further include art-recognized additives that aid or assist in the processing and/or performance of the compositions or articles. Non-limiting examples of such additives include photoinitiators, thermal initiators, polymerization inhibitors, solvents, light stabilizers (such as, but not limited to, ultraviolet light absorbers and light stabilizers, such as hindered amine light stabilizers (HALS)), heat stabilizers, mold release agents, rheology control agents, leveling agents (such as, but not limited to, surfactants), free radical scavengers, adhesion promoters (such as hexanediol diacrylate and coupling agents), and combinations and mixtures thereof.

The photochromic compounds of the present invention can be used in amounts (or ratios) such that the compositions, organic material or substrate (e.g., photochromic articles and photochromic coatings) into which the photochromic compounds are incorporated or otherwise connected exhibits desired optical properties. With some embodiments, the amount and types of photochromic material can be selected such that the composition, organic material or substrate is clear or colorless when the photochromic compound is in the closed-form (e.g., in the bleached or unactivated state), and can exhibit a desired resultant color when the photochromic compound (such as a photochromic indeno-fused phenanthrenopyran of the present invention) is in the open-form (e.g., when activated by actinic radiation). The precise amount of the photochromic material that is utilized in the various photochromic compositions and articles described herein is not critical provided that a sufficient amount is used to produce the desired effect. The particular amount of the photochromic material used can depend on a variety of factors, such as but not limited to the absorption characteristics of the photochromic compound, the color and intensity of the color desired upon activation, and the method used to incorporate or connect the photochromic material to the substrate. Photochromic compositions according to some embodiments of the present invention can include the photochromic material according to the present invention, including the compounds represented by Formula (Ia), (Ib), (IIa), or (IIb) in an amount of from 0.01 to 40 weight percent, or from 0.05 to 15, or from 0.1 to 5 weight percent, based on the weight of the photochromic composition. For purposes of further non-limiting illustration, the amount of the photochromic compound/material including the compounds represented by Formula (Ia), (Ib), (IIa), or (IIb) that is incorporated into an organic material can range from 0.01 to 40 weight percent, or from 0.05 to 15, or from 0.1 to 5 weight percent, based on the weight of the organic material.

The present invention also relates to photochromic articles that include one or more photochromic compounds according to the present invention, such as represented by Formula (Ia), (Ib), (IIa), and/or (IIb). The photochromic articles are, with some embodiments, prepared by art-recognized methods, such as by imbibition methods, cast-in-place methods, coating methods, in-mold coating methods, over-mold methods, and lamination methods.

With some embodiments, the photochromic articles are selected from ophthalmic articles, display articles, windows, mirrors, and active liquid crystal cell articles, and passive liquid crystal cell articles.

In accordance with some further embodiments, the photochromic articles of the present invention are ophthalmic articles, and the ophthalmic articles are selected from corrective lenses, non-corrective lenses, contact lenses, intraocular lenses, magnifying lenses, protective lenses, and visors.

With some additional embodiments, the photochromic articles of the present invention are display articles, and the display articles are selected from screens, monitors, and security elements.

The present invention can be further characterized by one or more of the following non-limiting clauses 1-12.

Clause 1: A photochromic compound having a core fused ring structure represented by at least one of the following Formula (Ia) or Formula (IIa),

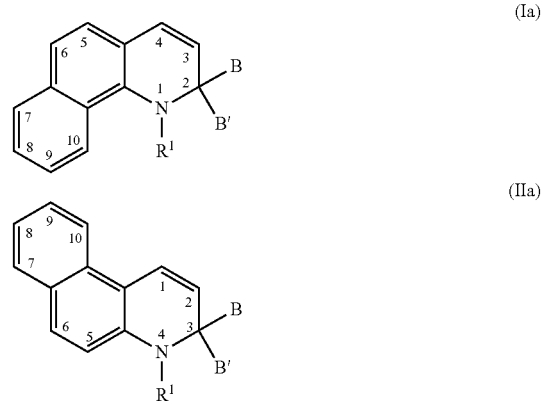

wherein independently for Formula (Ia) and Formula (IIa), $R^1$ is in each case independently selected from substituted or unsubstituted aryl, substituted or unsubstituted heteroaryl, —$SO_2R^5$, or —C(O)—$XR^5$, wherein X is selected from a single bond, —N($R^5$)—, or —O—, and $R^5$ in each case is independently selected from hydrogen, substituted or unsubstituted alkyl, substituted or unsubstituted aryl, or substituted or unsubstituted heteroaryl, and B and B' are each independently selected from substituted or unsubstituted alkenyl, substituted or unsubstituted alkynyl, substituted or unsubstituted aryl, or substituted or unsubstituted heteroaryl.

Clause 2: The photochromic compound of clause 1, wherein the photochromic compound is represented by at least one of the following Formula (Ib) or Formula (IIb),

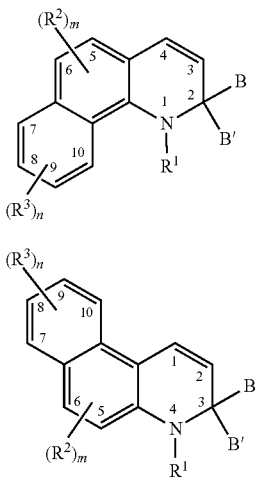

(Ib)

(IIb)

wherein independently for Formula (Ib) and Formula (IIb),
m in each case is independently 0 to 2
n in each case is independently 0 to 4,
$R^2$ independently for each m, and $R^3$ independently for each n, are each independently selected from the group consisting of:
hydroxyl;
cyano;
(meth)acrylate;
amino or nitrogen-containing heterocycle;
a halo group;
a perhalogenated group;
substituted or unsubstituted alkyl;
substituted or unsubstituted alkenyl;
substituted or unsubstituted alkynyl;
substituted or unsubstituted heterocycloalkyl;
substituted or unsubstituted aryl;
substituted or unsubstituted heteroaryl;
boronic acid or boronic acid ester;
substituted or unsubstituted alkoxy or substituted or unsubstituted aryloxy;
substituted or unsubstituted alkylthio or substituted or unsubstituted arylthio;
ketone, aldehyde, carboxylic acid ester, carboxylic acid, carboxylate, or amide;
carbonate, carbamate, or urea;
polyether, polyester, polycarbonate, or polyurethane; and
siloxy, alkoxysilane, or polysiloxane; or
two adjacent $R^2$ groups at position-5 and position-6 together form a substituted or unsubstituted fused benzene ring, or a substituted or unsubstituted fused indeno ring.

Clause 3: The photochromic compound of clauses 1 or 2, wherein
independently for $R^1$, each aryl substituent, and each heteroaryl substituent,
independently for $R^5$, each alkyl substituent, each aryl substituent, and each heteroaryl substituent, and
independently for $R^2$ and $R^3$, each alkyl substituent, each alkenyl substituent, each alkynyl substituent, each aryl substituent, each heterocycloalkyl substituent, each heteroaryl substituent, each alkoxy substituent, each aryloxy substituent, each alkylthio substituent, each arylthio substituent, each fused benzene ring substituent, and each fused indeno ring substituent,
is in each case independently selected from halo, cyano, nitro, alkyl, alkenyl, alkynyl, haloalkyl, perhaloalkyl, heterocycloalkyl, aryl, heteroaryl, hydroxyl, thiol, alkyl ether, alkyl thioether, aryl ether, aryl thioether, ketone, aldehyde, carboxylic acid ester, carboxylic acid, carboxylate, siloxy, alkoxysilane, polysiloxane, amide, amino, nitrogen-containing heterocycle, carbamate, carbonate, urea, polyester group, polyether group, polycarbonate group, polyurethane group, an acrylate group, a methacrylate group, combinations thereof, or two or more thereof.

Clause 4: The photochromic compound of any one of clauses 1 to 3, wherein B and B' are each independently selected from substituted or unsubstituted phenyl.

Clause 5: The photochromic compound of clause 4, wherein independently for B and B', each phenyl substituent is independently selected from alkyl, halo, perhaloalkyl, hydroxyl, thiol, alkyl ether, phenyl ether, alkyl thioether, phenyl thioether, morpholino, thiomorpholino, piperidino, piperazino, N-alkylpiperazino, or N-phenylpiperizino.

Clause 6: The photochromic compound of any one of clauses 1 to 5, wherein
$R^1$ is in each case independently selected from substituted or unsubstituted phenyl, and —C(O)—$XR^5$, wherein
X is selected from a single bond, —N($R^5$)—, or —O—, and
$R^5$ in each case is independently selected from hydrogen or substituted or unsubstituted phenyl,
wherein each phenyl substituent of $R^1$ and $R^5$ is in each case independently selected from the group consisting of halo, cyano, nitro, alkyl, alkenyl, alkynyl, haloalkyl, perhaloalkyl, heterocycloalkyl, aryl, heteroaryl, hydroxyl, thiol, alkyl ether, alkyl thioether, aryl thioether, ketone, aldehyde, carboxylic acid ester, carboxylic acid, carboxylate, siloxy, alkoxysilane, polysiloxane, amide, amino, nitrogen-containing heterocycle, carbamate, carbonate, urea, polyester group, polyether group, polycarbonate group, polyurethane group, an acrylate group, a methacrylate group, combinations thereof, and two or more thereof.

Clause 7: The photochromic compound of any one of clauses 2 to 6, wherein
each phenyl substituent of $R^1$ and $R^5$ is in each case independently selected from the group consisting of halo, alkyl, perhaloalkyl, and alkyl ether,
$R^2$ independently for each m, and $R^3$ independently for each n, are each independently selected from alkyl, perhaloalkyl, alkyl ether, unsubstituted phenyl, and phenyl substituted with at least one substituent selected from alkyl, perhaloalkyl, or alkyl ether, or
two adjacent $R^2$ groups at position-5 and position-6 together form a substituted or unsubstituted fused benzene ring, wherein each fused benzene ring substituent is independently selected from halo, alkyl, perhaloalkyl, or alkyl ether, and
B and B' are each independently selected from substituted or unsubstituted phenyl, wherein each phenyl substituent of B and B' is independently selected from halo, alkyl, perhaloalkyl, hydroxyl, alkyl ether, phenyl ether, morpholino, piperidino, piperazino, N-alkylpiperazino, or N-phenylpiperizino.

Clause 8: A photochromic compound represented by the following Formula (IV), $L^y$-(PC)$_{n'}$         Formula (IV)

wherein
n' is at least 2,
PC independently for each n' is a residue of the photochromic compound according to any one of clauses 1 to 7, and
L^y is a multivalent linking group selected from the group consisting of:
a first multivalent compound that is a multivalent polymer, and
a second multivalent compound that is different than the first multivalent compound, the second multivalent compound being non-polymeric and comprising a residue selected from the group consisting of, a residue of a polyisocyanate, a residue of a polyol, a residue of a polycarboxylic acid, a residue of a polycarbonate functional material, and combinations thereof.

Clause 9: A photochromic composition comprising the photochromic compound of any one of clauses 1 to 8.

Clause 10: A photochromic article comprising the photochromic compound of any one of clauses 1 to 8, wherein the photochromic article is selected from the group consisting of ophthalmic articles, display articles, windows, mirrors, active liquid crystal cell articles, and passive liquid crystal cell articles.

Clause 11: The photochromic article of clause 10, wherein the photochromic article is selected from ophthalmic articles, and the ophthalmic articles are selected from the group consisting of corrective lenses, non-corrective lenses, contact lenses, intra-ocular lenses, magnifying lenses, protective lenses, or visors.

Clause 12: The photochromic article of clause 10, wherein the photochromic article is selected from display articles, and the display articles are selected from the group consisting of screens, monitors, or security elements.

The present invention is more particularly described in the following examples, which are intended as illustrative only, since numerous modifications and variations therein will be apparent to those skilled in the art.

EXAMPLES

The following examples are provided in Parts 1 and 2, which are briefly summarized as follows. In Part 1, the synthesis of photochromic compounds according to the present invention is described in Examples 1-9, with comparative compounds described in Comparative Examples 10 and 11. In Part 2, the evaluation of the inventive photochromic and comparative compounds of Part 1 is described. In the following examples, "(v:v)" means (volume:volume).

Part 1: Synthesis of Photochromic Compounds

Example 1

Step 1

A solution of benzo[f]quinoline (20 g) in 400 ml of chloroform was cooled in ice/water bath for 10 minutes, then meta-chloroperoxybenzoic acid (33.48 g) in 600 ml of chloroform was added slowly via an addition funnel. The reaction mixture was stirred at room temperature for 4 hours, then washed with potassium carbonate solution. The organic phase was dried with anhydrous sodium sulfate and concentrated. The solid was collected by filtration and washed with hexane to give benzo[f]quinoline 4-oxide as pale yellow powder (18.4 g).

Step 2

To the product of Step 1 (12 g) in 200 ml of anhydrous tetrahydrofuran was added phenylmagnesium bromide in diethyl ether (88 ml, 264 mmol) dropwise at room temperature. The resulting reaction mixture was stirred at room temperature for 2 hours. A solution of ammonium chloride was added to the mixture to quench the excess base. Ethyl acetate was then added and the organic phase was separated and washed with brine, dried over anhydrous sodium sulfate, and concentrated. The residue was purified by silica gel chromatography using a 3:1 (v:v) hexane to ethyl acetate mixture to give 3-phenylbenzo[f]quinoline as pale white crystalline solid (6.0 g).

Step 3

The product of Step 2 (6.0 g) was dissolved in 300 ml of diethyl ether to which was added anhydrous 1,2-dimethoxyethane (7.4 ml) in one portion. Phenyllithium (37 ml) in diethyl ether was added dropwise via a syringe at room temperature and the mixture stirred overnight. Water was added, then extracted with ethyl acetate. The organic phase was dried over anhydrous sodium sulfate, concentrated, then purified by silica gel chromatography using a 3:1 (v:v) hexane to dichloromethane mixture to give 3,3-diphenyl-3,4-dihydrobenzo[f]quinoline as yellow crystalline solid (2 g).

Step 4

The product of Step 3 (0.333 g), 4-iodobenzotrifluoride (0.326 g), palladium acetate (0.0225 g), potassium tert-butoxide (0.336 g), tri-tert-butylphosphine (0.3 mL, 0.3 mmol), and 20 ml of anhydrous toluene were added to a flask under nitrogen, the mixture was sparged with nitrogen for 10 minutes, then heated to reflux for 2 hours. After cooling to room temperature, it was washed with water. The organic phase was dried with anhydrous sodium sulfate and concentrated. The residue was purified by silica gel chromatography using a 3:1 (v:v) hexane to dichloromethane mixture to give 3,3-diphenyl-4-(4-(trifluoromethyl)phenyl)-3,4-dihydrobenzo[f]quinoline as light yellow solid (0.1 g), which is represented by the following Formula E-1:

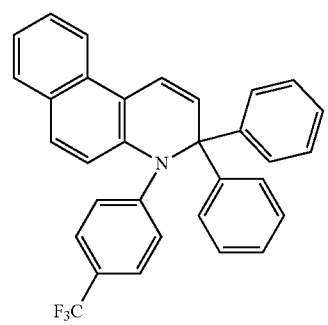

(E-1)

Example 2

Step 1

The procedures from Example 1 were followed except that in Step 4,4-iodoanisole was used in place of 4-iodobenzotrifluoride. The reaction mixture was purified by silica gel chromatography using a 3:1 (v:v) hexane to dichloromethane mixture to give 3,3-diphenyl-4-(4-methoxyphenyl)-3,4-dihydrobenzo[f]quinoline as light yellow solid, which is represented by the following Formula (E-2):

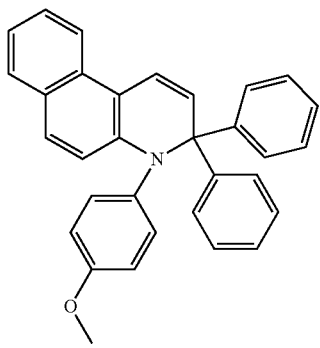

(E-2)

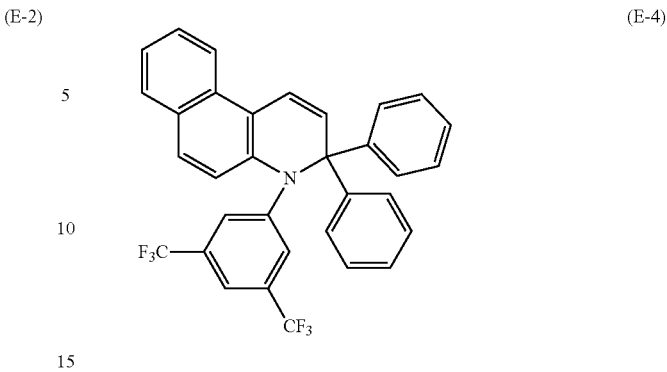

(E-4)

Example 3

Step 1

The product from Example 1 Step 3 (0.334 g) was dissolved in 15 ml anhydrous THF, then cooled in a dry ice/acetone bath for 15 minutes. n-Butyllithium (0.48 ml) was added dropwise. The mixture was stirred at −78° C. for 30 minutes, then benzoyl chloride (0.18 ml) was added. The mixture was stirred at room temperature overnight, then washed with water and brine. Organic phase was dried by anhydrous sodium sulfate and concentrated, the residue was purified by silica gel chromatography using a 3:1 (v:v) hexane to dichloromethane mixture to give (3,3-diphenyl-benzo[f]quinolin-4(3H)-yl)(phenyl)methanone as light yellow solid (0.12 g), which is represented by the following Formula (E-3):

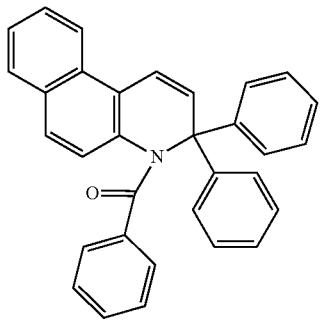

(E-3)

Example 4

Step 1

The procedures from Example 1 were followed except that in Step 4,1-iodo-3,5-bis(trifluoromethyl)benzene was used in place of 4-iodobenzotrifluoride. The reaction mixture was purified by silica gel chromatography using a 4:1 (v:v) hexane to dichloromethane mixture to give 4-(3,5-bis(trifluoromethyl)phenyl)-3,3-diphenyl-3,4-dihydrobenzo[f]quinoline as light brownish solid, which is represented by the following Formula (E-4):

Example 5

Step 1

The product of Step 1 of Example 1 (2 g) was dissolved in 40 ml of anhydrous tetrahydrofuran at room temperature, 4-methoxyphenylmagnesium bromide solution in diethyl ether (96 ml, 48 mmol) was added dropwise via an addition funnel, followed by stirring at room temperature for 2 hours. A solution of ammonium chloride was added to the mixture, then extracted with ethyl acetate. The organic phase was washed with brine and dried over anhydrous sodium sulfate and concentrated. The residue was purified by silica gel chromatography using a 4:1 (v:v) hexane to ethyl acetate mixture to give 3-(4-methoxyphenyl)benzo[f]quinoline as light brownish solid (0.65 g).

Step 2

The product of Step 1 (0.65 g) was dissolved in 200 ml of diethyl ether, anhydrous 1,2-dimethoxyethane (0.94 ml) was then added in one portion. Phenyllithium solution in diethyl ether (37 ml, 70.4 mmol) was added dropwise via a syringe at room temperature. The reaction mixture was stirred overnight. To the mixture was added water, and it was then extracted with ethyl acetate. The organic phase was separated, dried over anhydrous sodium sulfate and concentrated. The residue was purified by silica gel chromatography using a 7:3 (v:v) hexane to dichloromethane mixture to give 3-(4-methoxyphenyl)-3-phenyl-3,4-dihydrobenzo[f] quinoline as brownish solid (0.2 g).

Step 3

The product of Step 2 (0.2 g), 4-iodobenzotrifluoride (0.21 g), palladium acetate (0.019 g), potassium tert-butoxide (0.185 g), tri-tert-butylphosphine (0.33 mL, 0.33 mmol), and 20 ml of toluene were added to a flask under nitrogen, the mixture was sparged with nitrogen for 10 minutes, then heated to reflux overnight. After cooling to room temperature, it was washed with water. The organic phase was dried with anhydrous sodium sulfate and concentrated. The residue was purified by silica gel chromatography using a 4:1 (v:v) hexane to dichloromethane mixture to give 3-(4-methoxyphenyl)-3-phenyl-4-(4-(trifluoromethyl)phenyl)-3, 4-dihydrobenzo[f]quinoline as greenish yellow solid (0.14 g), which is represented by the following Formula (E-5):

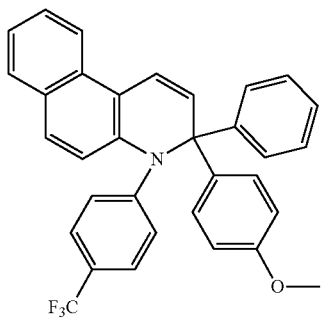

(E-5)

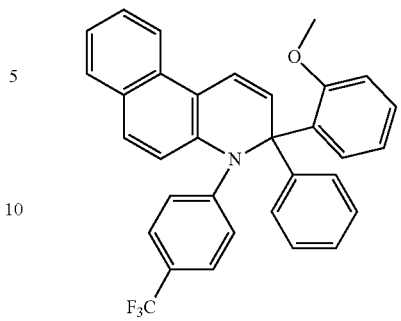

(E-6)

Example 6

Step 1

The product of Example 1 Step 1 (1 g) was dissolved in 20 ml anhydrous tetrahydrofuran at room temperature, 2-methoxyphenylmagnesium bromide solution in diethyl ether (25.6 ml, 25.6 mmol) was added dropwise. The mixture was stirred at room temperature overnight. A solution of ammonium chloride was added to the mixture followed by extraction with ethyl acetate. The organic phase was washed with brine, dried over anhydrous sodium sulfate and concentrated. The residue was purified by silica gel chromatography using a 4:1 (v:v) hexane to ethyl acetate mixture to give 3-(2-methoxyphenyl)benzo[f]quinoline as green solid (0.8 g).

Step 2

The product of Step 1 (0.8 g) was dissolved in 20 ml diethyl ether. Phenyllithium solution in diethyl ether (7.9 ml, 15.6 mmol) was added dropwise at room temperature. The reaction mixture was stirred overnight. To the mixture was added water, then extracted with ethyl acetate. The organic phase was separated, dried over anhydrous sodium sulfate, and concentrated. The residue was purified by silica gel chromatography using a 7:3 (v:v) hexane to dichloromethane mixture to give 3-(2-methoxyphenyl)-3-phenyl-3,4-dihydrobenzo[f]quinoline as light yellow solid (0.25 g).

Step 3

The product of Step 2 (0.20 g), 4-iodobenzotrifluoride (0.21 g), palladium acetate (0.019 g), potassium tert-butoxide (0.185 g), tri-tert-butylphosphine (0.33 mL, 0.33 mmol), and 20 ml of anhydrous toluene were added to a flask under nitrogen, the mixture was sparged with nitrogen for 10 minutes, then heated to reflux overnight. After cooling to room temperature, it was washed with water, dried with anhydrous sodium sulfate and concentrated. The residue was purified by silica gel chromatography using a 4:1 (v:v) hexane to dichloromethane mixture to give 3-(2-methoxyphenyl)-3-phenyl-4-(4-(trifluoromethyl)phenyl)-3,4-dihydrobenzo[f] quinoline as yellow solid (0.07 g), which is represented by the following Formula (E-6):

Example 7

Step 1

The product of Example 6 Step 2 (0.22 g) was dissolved in 10 ml anhydrous tetrahydrofuran, then cooled in dry ice/acetone bath for 15 minutes. n-Butyllithium (0.46 ml, 1.2 mmol) was added dropwise. The mixture was stirred at −78° C. for 30 minutes, then benzoyl chloride (0.11 ml) was added. The mixture was stirred at room temperature overnight. The mixture was then washed with water and brine, dried with anhydrous sodium sulfate and concentrated. The residue was purified by silica gel chromatography using a 4:1 (v:v) hexane to ethyl acetate mixture to give (3-(2-methoxyphenyl)-3-phenylbenzo[f]quinolin-4(3H)-yl)(phenyl)methanone as light brown solid (0.12 g), which is represented by the following Formula (E-7):

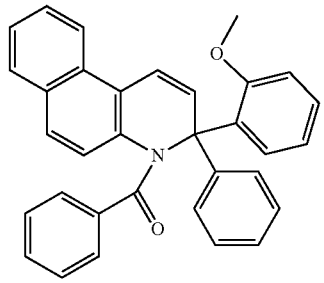

(E-7)

Example 8

Step 1

1-bromo-4-(trifluoromethyl)benzene (4.76 g) was dissolved in anhydrous diethyl ether, the mixture was cooled to −30° C. for 15 minutes. A solution of n-butyllithium in hexane (21.15 mmol) was then added dropwise, the mixture was warmed to room temperature and stirred at room temperature for 1 hour. The reaction mixture was used as is for the next step reaction below.

Step 2

The product of Example 1 Step 2 (1.08 g) was dissolved in 20 ml of diethyl ether; anhydrous 1,2-dimethoxyethane (2.2 ml) was added in one portion. The product of Step 1 (21.15 mmol) in diethyl ether was added dropwise at room temperature, then stirred overnight. To the mixture was added water, and then extracted with ethyl acetate. The organic phase was dried over anhydrous sodium sulfate, and concentrated, then purified by silica gel chromatography using a 3:1 (v:v) hexane to dichloromethane mixture to give 3-phenyl-3-(4-(trifluoromethyl)phenyl)-3,4-dihydrobenzo[f]quinoline as orange solid (0.43 g).

Step 3

The product of Step 2 (0.26 g), 4-iodobenzotrifluoride (0.25 g), palladium acetate (0.022 g), potassium tert-butoxide (0.22 g), and 30 ml of anhydrous toluene were added to a flask under nitrogen, the mixture was sparged with nitrogen for 10 minutes, and tri-tert-butylphosphine (0.39 mL, 0.39 mmol) solution in toluene was added followed by heating at reflux overnight. After cooling to room temperature, the solution was washed with water, dried with anhydrous sodium sulfate, concentrated, and the residue purified by silica gel chromatography using a 4:1 (v:v) hexane to dichloromethane mixture to give 3-phenyl-3-(4-(trifluoromethyl)phenyl)4-(4-(trifluoromethyl)phenyl)-3,4-dihydrobenzo[f]quinoline bright yellow solid (0.15 g), which is represented by the following Formula (E-8):

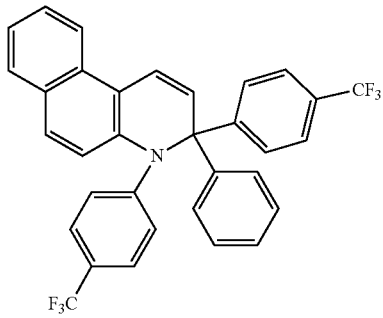

(E-8)

Example 9

Step 1

3-hydroxy-2-methylpyridine (25 g) and N-Phenyl-bis(trifluoromethanesulfonimide) (82.36 g) were dissolved in 760 ml of dichloromethane, then cooled in ice/water bath for 15 minutes. Triethylamine was added, the mixture was stirred at room temperature for 13 hours. The reaction mixture was washed with 1N sodium hydroxide solution twice then washed with brine and dried with anhydrous sodium sulfate. The solvent was removed to give 2-methylpyridin-3-yl trifluoromethanesulfonate as brown oil (53.9 g).

Step 2

The product of Step 1 (24.12 g), tetrakis(triphenylphosphine)palladium (4.6 g), 2-formyl-4-methoxyphenylboronic acid (18.18 g), toluene (300 ml), and methanol (150 ml) were added into a 1 L flask. The mixture was sparged with nitrogen gas for 15 minutes. Another solution of sodium carbonate (21.2 g) in 150 ml of water was sparged with nitrogen gas for 15 minutes, then added to the first solution via cannula. The reaction mixture was heated to 90° C. in oil bath for 15 hours under nitrogen. After the reaction mixture was cooled to room temperature, it was washed with water and brine, dried with anhydrous sodium sulfate and the solution was loaded to a plug column and eluted with a 3:1 (v:v) hexane to ethyl acetate mixture to give 5-methoxy-2-(2-methylpyridin-3-yl)benzaldehyde as pale solid (18.38 g).

Step 3

The product of Step 2 (18.18 g) was dissolved in 76 ml anhydrous dimethylformamide and the solution was cooled at ice/water bath for 10 minutes. A solution of potassium tert-butoxide (17 g) in 152 ml anhydrous dimethylformamide was added to above solution slowly at 0° C. while stirring. After addition was completed, the mixture was stirred at room temperature overnight. To the mixture was added 150 ml water, and extracted with dichloromethane (4×150 ml). Organic phase was combined and dried with anhydrous sodium sulfate. Solvent was removed under vacuum, the residue was dissolved in chloroform and purified with plug silica gel column, eluted with a 1:1 (v:v) hexane to ethyl acetate mixture to give 8-methoxybenzo[f]quinoline as light brown solid (15.84 g).

Step 4

The product of Step 3 (10 g) was dissolved in 200 ml of chloroform and the solution was cooled in ice/water bath for 10 minutes, then meta-chloroperoxybenzoic acid (12.37 g, 71.68 mmol) in 300 ml of chloroform was added slowly. The reaction mixture was stirred at room temperature for 4 hours, then washed with potassium carbonate solution and brine, dried with anhydrous sodium sulfate and concentrated. The solid was collected by filtration and washed with hexane to give 8-methoxybenzo[f]quinoline 4-oxide as brown solid (8 g).

Step 5

The product of Step 4 (4.0 g) was dissolved in 80 ml anhydrous tetrahydrofuran at room temperature, 2-methoxyphenylmagnesium bromide solution (71.0 ml, 71.0 mmol) in diethyl ether was added dropwise via a syringe. After addition was completed, the reaction mixture was stirred at room temperature for overnight. A solution of ammonium chloride was added to the mixture to quench the excess base. Ethyl acetate was then added and the organic phase was separated and washed with brine, dried over anhydrous sodium sulfate and concentrated. The residue was purified by silica gel chromatography with a 85:15 (v:v) hexane to ethyl acetate to give 3-(2-methoxyphenyl)-8-methoxybenzo[f]quinoline as light brown solid (1.82 g).

Step 6

The product of Step 5 (1.82 g) was dissolved in 200 ml of diethyl ether, anhydrous 1,2-dimethoxyethane (1.8 ml) was then added in one portion. Phenyllithium (9.2 ml, 8.66 mmol) in diethyl ether was added dropwise at room temperature. The reaction mixture was stirred at room temperature for 8 hours. Water was added to the mixture, and it was extracted with ethyl acetate. The organic phase was separated, dried over anhydrous sodium sulfate, and concentrated, then purified by silica gel chromatography with a 3:2 (v:v) hexane to dichloromethane to give 8-methoxy-3-(2-methoxyphenyl)-3-phenyl-3,4-dihydrobenzo[f]quinoline as brownish yellow solid (0.5 g).

Step 7

The product of Step 6 (0.26 g), 4-iodobenzotrifluoride (0.27 g), palladium acetate (0.023 g), potassium tert-butoxide (0.23 g), tri-tert-butylphosphine (0.4 mL, 0.4 mmol), and 20 ml of anhydrous toluene were added to a flask under nitrogen, and sparged with nitrogen for 15 minutes, followed by heating at reflux for 14 hours. After cooling to room temperature, the mixture was washed with water, dried with anhydrous sodium sulfate, concentrated, and the residue was purified by silica gel chromatography, eluted with a 3:2 (v:v) hexane to dichloromethane to give 8-methoxy-3-(2-methoxyphenyl)-3-phenyl-4-(4-(trifluoromethyl)phenyl)-3,4-dihydrobenzo[f]quinoline as yellowish solid (0.09 g), which is represented by the following Formula (E-9):

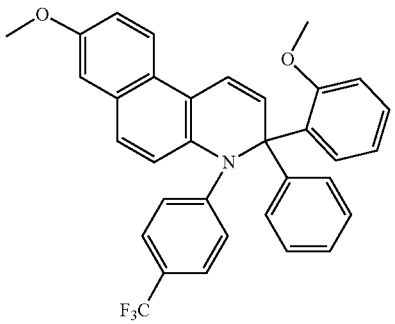

(E-9)

Comparative Example 10

The product of step 2 of Example 6,3-(2-methoxyphenyl)-3-phenyl-3,4-dihydrobenzo[f]quinoline, was used as the compound of the present Comparative Example 10, which is represented by the following Formula (CE-10):

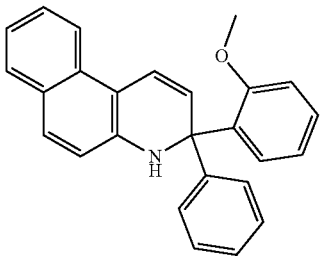

(CE-10)

Comparative Example 11

The material, 3-(2,4-dimethoxyphenyl)-3-(4-methoxyphenyl)-3H-benzo[f]chromene, was used as the photochromic compound of the present Comparative Example 11, which is represented by the following Formula (CE-11):

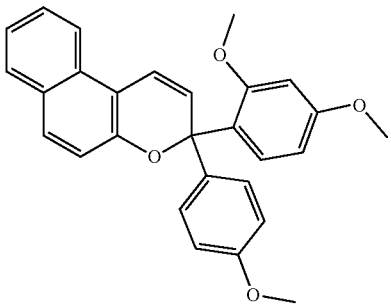

(CE-11)

Part 2: Evaluation of Photochromic Compounds

The photochromic compounds of Examples 6 and 9, and Comparative Examples 10 and 11 (CE10 and CE11), were each incorporated into a separate polyurethane coating system as described in Examples 1-3 of U.S. Pat. No. 8,608,988 B2, at the same mol %, and applied at the same coating thickness to 2"×2" test chips made from CR-39® monomer (PPG Industries, Inc.). All coated test chips were cured at 125° C. for 1 hour.

Each of the coated test chips was conditioned by first being exposed to 365 nanometer ultraviolet light for 10 minutes at a distance of about 14 centimeters to activate the photochromic compounds within the coating. The UVA (315 to 380 nm) irradiance at the chip was measured with a LICOR® Model Li-1800 spectroradiometer, and found to be 22.2 watts per square meter. Each of the test chips was then placed under a 500 watt, high intensity halogen lamp for 10 minutes at a distance of about 36 centimeters, to bleach (inactivate) the photochromic compounds. The illuminance at chip was measured with the LICOR® spectroradiometer and found to be 21.9 Klux. The coated test chips then were kept in a dark environment at ambient room temperature (i.e., from 70° F. to 75° F.; 21° C. to 24° C.) for at least 1 hour prior to testing on an optical bench. Prior to optical bench measurement, the coated test chips were measured for ultraviolet absorbance at 390 nanometers. The unactivated percent transmission (%T) for Examples 6 and 9, and for each comparative examples CE10 and CE11 was determined using the CIE Y value in accordance with CIE 15: 2004 colorimetry using a D 65 illuminant and 10° observer. The a* and b* values as used in the present examples refers to the a* and b* values measured in accordance with CIE 15: 2004 space colorimetry, employing a D 65 illuminant and 10° observer, using a Hunter UltraScan Pro unit.

The BMP optical bench was fitted with two 150-watt ORIEL® Model #66057 Xenon arc lamps at right angles to each other. The light path from Lamp 1 was directed through a 3 mm SCFIOTT® KG-2 band-pass filter and appropriate neutral density filters that contributed to the required UV and partial visible light irradiance level. The light path from Lamp 2 was directed through a 3 mm SCFIOTT® KG-2 band-pass filter, a SCFIOTT® short band 400 nm cutoff filter and appropriate neutral density filters in order to provide supplemental visible light illuminance. A 2 inch×2 inch (5.1 cm×5.1 cm) 50% polka dot beam splitter, at 45° to each lamp was used to mix the two beams. The combination of neutral density filters and voltage control of the Xenon arc lamp were used to adjust the intensity of the irradiance. Proprietary software (i.e., BMPSoft version 2.1e) was used on the BMP to control timing, irradiance, air cell and sample temperature, shuttering, filter selection and response measurement. A ZEISS® spectrophotometer, Model MCS 501, with fiber optic cables for light delivery through the coated test chip was used for response and color measurement. Photopic response measurements were collected on each coated test chip. The power output of the optical bench (i.e., the dosage of light that the coated test chip was exposed to) was adjusted to 6.7 Watts per square meter (W/m²) UVA, integrated from 315-380 nm and 50 Klux illuminance, integrated from 380-780 nm. Measurement of this power set-point was made using an irradiance probe and the calibrated Zeiss spectrophotometer. The coated test chip sample cell was fitted with a quartz window and self-centering sample holder. The temperature in the sample cell was controlled at 23° C. through the software with a modified Facis, Model FX-10, environment simulator. Measurement of the sample's dynamic photochromic response and color measurements was made using the same Zeiss spectrophotometer, with fiber optic cables for light delivery from a tungsten halogen lamp and through the sample. The collimated monitoring light beam from the fiber optic cable was maintained perpendicular to the test sample while passing through the sample and directed into a receiving fiber optic cable assembly attached to the spectrophotometer. The exact point of placement of the sample in the sample cell was where the activating xenon arc beam and the monitoring light beam intersected to form two concentric circles of light. The angle of incidence of the xenon arc beam at the sample placement point was 30° from perpendicular.

The $\lambda_{max-vis}$ is the wavelength in the visible spectrum at which the maximum absorption of the activated form of the photochromic compound occurs. The change in optical density ($\Delta$OD) from the bleached state to the darkened state was determined by establishing the initial transmittance at $\lambda_{max-vis}$, opening the shutter from the Xenon lamp to provide ultraviolet radiation to change the test lens from the bleached state to an activated (i.e., darkened) state. Data was collected at selected intervals of time, measuring the transmittance at the $\lambda_{max-vis}$, and calculating the change in optical density according to the formula: $\Delta OD = \log(\%Tb/\%Ta)$, where %Tb is the percent transmittance in the bleached state, %Ta is the percent transmittance in the activated state and the logarithm is to the base 10. The $\Delta$OD $\lambda_{max-vis}$ at saturation is after 15 minutes of activation and the Fade Half-Life ("Fade T1/2") value is the time interval in seconds for the $\Delta$OD $\lambda_{max-vis}$ of the activated form of the photochromic compound in the coating to reach one half the fifteen minute $\Delta$OD $\lambda_{max-vis}$ at 73.4° F. (23° C.), after removal of the activating light source. The results of photochromic performance testing are summarized in the following Table 1.

TABLE 1

Results of Photochromic Performance Testing of Coatings

| Photochromic Compound | Net 390 nm Abs | Unactivated % T | a* | b* | Activated at 23° C. $\Delta$OD | $\lambda_{max-vis}$ (nm) | Fade T½ (sec) |
|---|---|---|---|---|---|---|---|
| Example 6 | 0.95 | 91.4 | −1.5 | 3.6 | 0.82 | 439 | 177 |
| Example 9 | 1.07 | 91.4 | −3.5 | 7.7 | 1.13 | 462 | 329 |
| CE10 | 0.57 | 90.9 | −2.1 | 7.8 | Did not demonstrate photochromic behavior | | |
| CE11 | 0.07 | 91.5 | 0.0 | 1.3 | 0.45 | 485 | 174 |

The photochromic compounds of Examples 6 and 9 provided similar fade and bleach color results relative to that of the photochromic compound of Comparative Example 11 (CE11). The photochromic compounds of Examples 6 and 9 also provided more intense absorption at λmax-vis relative to that of the photochromic compound of Comparative Example 11 (CE11), which is desirable with photochromic articles, such as photochromic ophthalmic lenses, with regard to providing a combination of satisfactory darkness outdoors (when exposed to actinic radiation) and fast fade to clarity indoors (in the absence of exposure to actinic radiation).

With the remaining photochromic compounds of Examples 1 through 5, 7, and 8, approximately 1 mg of each photochromic compound thereof was separately dissolved in 2 ml of ethyl acetate, and each solution was activated with a 365 nm bulb using a Spectroline ENF-280C lamp. The photochromic compounds of Examples 1 through 5, 7, and 8 (as tested in the ethyl acetate solutions) were each observed to demonstrate photochromic properties, and were each further observed to provide fade half-life values (Fade T1/2) of less than 2 seconds.

The present invention has been described with reference to specific details of particular embodiments thereof. It is not intended that such details be regarded as limitations upon the scope of the invention except insofar as to the extent that they are included in the accompanying claims.

What is claimed is:

1. A photochromic compound having a core fused ring structure represented by at least one of the following Formula (Ia) or Formula (IIa),

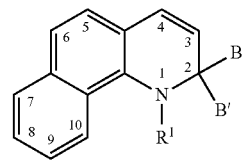
(Ia)

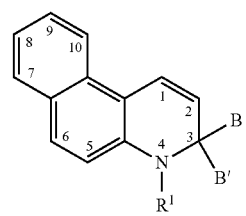
(IIa)

wherein independently for Formula (Ia) and Formula (IIa),
  $R^1$ is in each case independently selected from substituted or unsubstituted aryl, substituted or unsubstituted heteroaryl, —SO$_2$R$^5$, or —C(O)—XR$^5$, wherein,
  X is selected from a single bond, —N(R$^5$)—, or —O—, and
  $R^5$ in each case is independently selected from hydrogen, substituted or unsubstituted alkyl, substituted or unsubstituted aryl, or substituted or unsubstituted heteroaryl, and
  B and B' are each independently selected from substituted or unsubstituted alkenyl, substituted or unsubstituted alkynyl, substituted or unsubstituted aryl, or substituted or unsubstituted heteroaryl.

2. The photochromic compound of claim 1, wherein the photochromic compound is represented by at least one of the following Formula (Ib) or Formula (IIb),

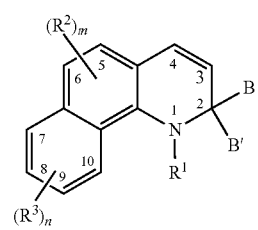
(Ib)

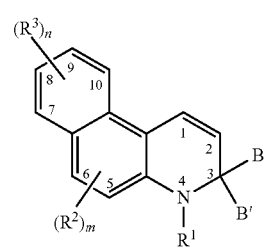
(IIb)

wherein independently for Formula (Ib) and Formula (IIb),
  m in each case is independently 0 to 2,
  n in each case is independently 0 to 4, R² independently for each m, and R³ independently for each n, are each independently selected from the group consisting of:
hydroxyl;
cyano;
(meth)acrylate;
amino or nitrogen-containing heterocycle;
a halo group;
a perhalogenated group;
substituted or unsubstituted alkyl;
substituted or unsubstituted alkenyl;
substituted or unsubstituted alkynyl;
substituted or unsubstituted heterocycloalkyl;
substituted or unsubstituted aryl;
substituted or unsubstituted heteroaryl;
boronic acid or boronic acid ester;
substituted or unsubstituted alkoxy or substituted or unsubstituted aryloxy;
substituted or unsubstituted alkylthio or substituted or unsubstituted arylthio;
ketone, aldehyde, carboxylic acid ester, carboxylic acid, carboxylate, or amide;
carbonate, carbamate, or urea;
polyether, polyester, polycarbonate, or polyurethane; and
siloxy, alkoxysilane, or polysiloxane; or
two adjacent R² groups at position-5 and position-6 together form a substituted or unsubstituted fused benzene ring, or a substituted or unsubstituted fused indeno ring.

3. The photochromic compound of claim 1, wherein
independently for R¹, each aryl substituent, and each heteroaryl substituent,
independently for R⁵, each alkyl substituent, each aryl substituent, and each heteroaryl substituent, and
independently for R² and R³, each alkyl substituent, each alkenyl substituent, each alkynyl substituent, each aryl substituent, each heterocycloalkyl substituent, each heteroaryl substituent, each alkoxy substituent, each aryloxy substituent, each alkylthio substituent, each arylthio substituent, each fused benzene ring substituent, and each fused indeno ring substituent,
is in each case independently selected from halo, cyano, nitro, alkyl, alkenyl, alkynyl, haloalkyl, perhaloalkyl, heterocycloalkyl, aryl, heteroaryl, hydroxyl, thiol, alkyl ether, alkyl thioether, aryl ether, aryl thioether, ketone, aldehyde, carboxylic acid ester, carboxylic acid, carboxylate, siloxy, alkoxysilane, polysiloxane, amide, amino, nitrogen-containing heterocycle, carbamate, carbonate, urea, polyester group, polyether group, polycarbonate group, polyurethane group, an acrylate group, a methacrylate group, combinations thereof, or two or more thereof.

4. The photochromic compound of claim 2, wherein B and B' are each independently selected from substituted or unsubstituted phenyl.

5. The photochromic compound of claim 4, wherein independently for B and B', each phenyl substituent is independently selected from alkyl, halo, perhaloalkyl, hydroxyl, thiol, alkyl ether, phenyl ether, alkyl thioether, phenyl thioether, morpholino, thiomorpholino, piperidino, piperazino, N-alkylpiperazino, or N-phenylpiperizino.

6. The photochromic compound of claim 3, wherein
R¹ is in each case independently selected from substituted or unsubstituted phenyl, and —C(O)—XR⁵, wherein
X is selected from a single bond, —N(R⁵)—, or —O—, and
R⁵ in each case is independently selected from hydrogen or substituted or unsubstituted phenyl,
wherein each phenyl substituent of R¹ and R⁵ is in each case independently selected from the group consisting of halo, cyano, nitro, alkyl, alkenyl, alkynyl, haloalkyl, perhaloalkyl, heterocycloalkyl, aryl, heteroaryl, hydroxyl, thiol, alkyl ether, alkyl thioether, aryl thioether, ketone, aldehyde, carboxylic acid ester, carboxylic acid, carboxylate, siloxy, alkoxysilane, polysiloxane, amide, amino, nitrogen-containing heterocycle, carbamate, carbonate, urea, polyester group, polyether group, polycarbonate group, polyurethane group, an acrylate group, a methacrylate group, combinations thereof, and two or more thereof.

7. The photochromic compound of claim 6, wherein
each phenyl substituent of R¹ and R⁵ is in each case independently selected from the group consisting of halo, alkyl, perhaloalkyl, and alkyl ether,
R² independently for each m, and R³ independently for each n, are each independently selected from alkyl, perhaloalkyl, alkyl ether, unsubstituted phenyl, and phenyl substituted with at least one substituent selected from alkyl, perhaloalkyl, or alkyl ether, or
two adjacent R² groups at position-5 and position-6 together form a substituted or unsubstituted fused benzene ring, wherein each fused benzene ring substituent is independently selected from halo, alkyl, perhaloalkyl, or alkyl ether, and
B and B' are each independently selected from substituted or unsubstituted phenyl, wherein each phenyl substituent of B and B' is independently selected from halo, alkyl, perhaloalkyl, hydroxyl, alkyl ether, phenyl ether, morpholino, piperidino, piperazino, N-alkylpiperazino, or N-phenylpiperizino.

8. A photochromic composition comprising the photochromic compound of claim 1.

9. A photochromic article comprising the photochromic compound of claim 1, wherein the photochromic article is selected from the group consisting of ophthalmic articles, display articles, windows, mirrors, active liquid crystal cell articles, and passive liquid crystal cell articles.

10. The photochromic article of claim 9, wherein the photochromic article is selected from ophthalmic articles, and the ophthalmic articles are selected from the group consisting of corrective lenses, non-corrective lenses, contact lenses, intra-ocular lenses, magnifying lenses, protective lenses, or visors.

11. The photochromic article of claim 9, wherein the photochromic article is selected from display articles, and the display articles are selected from the group consisting of screens, monitors, or security elements.

12. The photochromic compound of claim 2, wherein
independently for R¹, each aryl substituent, and each heteroaryl substituent,
independently for R⁵, each alkyl substituent, each aryl substituent, and each heteroaryl substituent, and
independently for R² and R³, each alkyl substituent, each alkenyl substituent, each alkynyl substituent, each aryl substituent, each heterocycloalkyl substituent, each heteroaryl substituent, each alkoxy substituent, each aryloxy substituent, each alkylthio substituent, each arylthio substituent, each fused benzene ring substituent, and each fused indeno ring substituent,
is in each case independently selected from halo, cyano, nitro, alkyl, alkenyl, alkynyl, haloalkyl, perhaloalkyl, heterocycloalkyl, aryl, heteroaryl, hydroxyl, thiol, alkyl ether, alkyl thioether, aryl ether, aryl thioether, ketone, aldehyde, carboxylic acid ester, carboxylic acid, carboxylate, siloxy, alkoxysilane, polysiloxane, amide, amino, nitrogen-containing heterocycle, carbamate, carbonate, urea, polyester group, polyether group, polycarbonate group, polyurethane group, an acrylate group, a methacrylate group, combinations thereof, or two or more thereof.

13. The photochromic compound of claim 12, wherein $R^1$ is in each case independently selected from substituted or unsubstituted phenyl, and —C(O)—$XR^5$, wherein X is selected from a single bond, —N($R^5$)—, or —O—, and $R^5$ in each case is independently selected from hydrogen or substituted or unsubstituted phenyl, wherein each phenyl substituent of $R^1$ and $R^5$ is in each case independently selected from the group consisting of halo, cyano, nitro, alkyl, alkenyl, alkynyl, haloalkyl, perhaloalkyl, heterocycloalkyl, aryl, heteroaryl, hydroxyl, thiol, alkyl ether, alkyl thioether, aryl thioether, ketone, aldehyde, carboxylic acid ester, carboxylic acid, carboxylate, siloxy, alkoxysilane, polysiloxane, amide, amino, nitrogen-containing heterocycle, carbamate, carbonate, urea, polyester group, polyether group, polycarbonate group, polyurethane group, an acrylate group, a methacrylate group, combinations thereof, and two or more thereof.

14. The photochromic compound of claim 13, wherein
each phenyl substituent of $R^1$ and $R^5$ is in each case independently selected from the group consisting of halo, alkyl, perhaloalkyl, and alkyl ether, $R^2$ independently for each m, and $R^3$ independently for each n, are each independently selected from alkyl, perhaloalkyl, alkyl ether, unsubstituted phenyl, and phenyl substituted with at least one substituent selected from alkyl, perhaloalkyl, or alkyl ether, or two adjacent $R^2$ groups at position-5 and position-6 together form a substituted or unsubstituted fused benzene ring, wherein each fused benzene ring substituent is independently selected from halo, alkyl, perhaloalkyl, or alkyl ether, and B and B' are each independently selected from substituted or unsubstituted phenyl, wherein each phenyl substituent of B and B' is independently selected from halo, alkyl, perhaloalkyl, hydroxyl, alkyl ether, phenyl ether, morpholino, piperidino, piperazino, N-alkylpiperazino, or N-phenylpiperizino.

* * * * *

UNITED STATES PATENT AND TRADEMARK OFFICE
CERTIFICATE OF CORRECTION

PATENT NO. : 12,404,448 B2
APPLICATION NO. : 17/763713
DATED : September 2, 2025
INVENTOR(S) : Robert W. Walters It is certified that error appears in the above-identified patent and that said Letters Patent is hereby corrected as shown below:

In the Claims

Column 33, Line 64, Claim 5, delete "N-phenylpiperizino." and insert -- N-phenylpiperazino. --

Column 34, Line 36, Claim 7, delete "N-phenylpiperizino." and insert -- N-phenylpiperazino. --

Column 36, Line 24, Claim 14, delete "N-phenylpiperizino." and insert -- N-phenylpiperazino. --

Signed and Sealed this
Eighteenth Day of November, 2025

John A. Squires
*Director of the United States Patent and Trademark Office*